(12) United States Patent
Chadha et al.

(10) Patent No.: US 10,034,913 B2
(45) Date of Patent: Jul. 31, 2018

(54) ANTI-ANGIOGENIC PEPTIDES AND USES THEREOF

(71) Applicant: Health Research, Inc., Buffalo, NY (US)

(72) Inventors: Kailash C. Chadha, Williamsville, NY (US); Gary J. Smith, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 14/817,648

(22) Filed: Aug. 4, 2015

(65) Prior Publication Data

US 2016/0051623 A1 Feb. 25, 2016

Related U.S. Application Data

(62) Division of application No. 14/235,563, filed as application No. PCT/US2012/047803 on Jul. 23, 2012, now abandoned.

(60) Provisional application No. 61/513,019, filed on Jul. 29, 2011.

(51) Int. Cl.
| | | |
|---|---|---|
| A61K 38/00 | (2006.01) | |
| A61K 35/00 | (2006.01) | |
| C07K 14/515 | (2006.01) | |
| A61K 38/12 | (2006.01) | |
| A61K 38/10 | (2006.01) | |
| A61K 38/16 | (2006.01) | |
| A61K 38/08 | (2006.01) | |
| C07K 14/47 | (2006.01) | |
| C07K 7/06 | (2006.01) | |
| C07K 7/08 | (2006.01) | |

(52) U.S. Cl.
CPC ............... *A61K 38/10* (2013.01); *A61K 38/08* (2013.01); *A61K 38/12* (2013.01); *C07K 7/06* (2013.01); *C07K 7/08* (2013.01); *C07K 14/47* (2013.01); *A61K 38/00* (2013.01)

(58) Field of Classification Search
None
See application file for complete search history.

(56) References Cited

U.S. PATENT DOCUMENTS

| | | |
|---|---|---|
| 5,807,978 A | 9/1998 | Kokolus et al. |
| 6,413,513 B1 | 7/2002 | Holaday et al. |
| 2005/0054575 A1 | 3/2005 | Schlom et al. |

OTHER PUBLICATIONS

"Angiogenesis", available online at http://medical-dictionary.thefreedictionary.com/angiogenesis, 3 pages (accessed on Sep. 22, 2016).*
"Cell Migration", available online at http://www.biology-online.org/dictionary/Cell_migration, 1 page (accessed on Sep. 22, 2016).*
UniProt Database, Accession No. P07288, 16 pages (last sequence update Jul. 1, 1989).*
Aalinkeel, R., et al., Role of Prostate-Specific Antigen (PSA) in Pathological Angiogenesis and Prostate Tumor Growth, Horizons in Cancer Research, 2010, vol. 42, Chapter 2, pp. 1-37.
Aalinkeel, R., et al., Overexpression of MMP-9 Contributes to Invasiveness of Prostate Cancer Line LNCaP, Immunological Investigations, 2011, vol. 40, pp. 447-464.
Chadha K., et al., Enzymatic Activity of Free-Prostate-Specific Antigen (f-PSA) Is Not Required for Some of its Physiological Activities, The Prostate, 2011, vol. 71, pp. 1680-1690.
GenBank EAW71924—kallikrien 3, (prostate specific antigen), isoform CRA_c [*Homo sapiens*], Dec. 18, 2006, URL:http://www.ncbi.nlm.nih.gov/protein/EAW71924.
Fortier, A. H. et al., Recombinant prostate specific antigen inhibits angiogenesis in vitro and in vivo. Prostate. Aug. 1, 2003, vol. 56, No. 3, pp. 212-219. See pp. 214-217.
UniProt Database, Accession No. P07288, 12 pages (sequence last updated Jul. 1, 1989).

* cited by examiner

*Primary Examiner* — Hasan Ahmed
*Assistant Examiner* — Thea D'Ambrosio
(74) *Attorney, Agent, or Firm* — Hodgson Russ LLP

(57) ABSTRACT

Provided are peptide sequences derived from prostate serum antigen (PSA). The peptides are provided in cyclic and linear form. Methods for using the peptides for inhibition of angiogenesis, such as angiogenesis in a tumor, are provided.

5 Claims, 21 Drawing Sheets

Figure 1
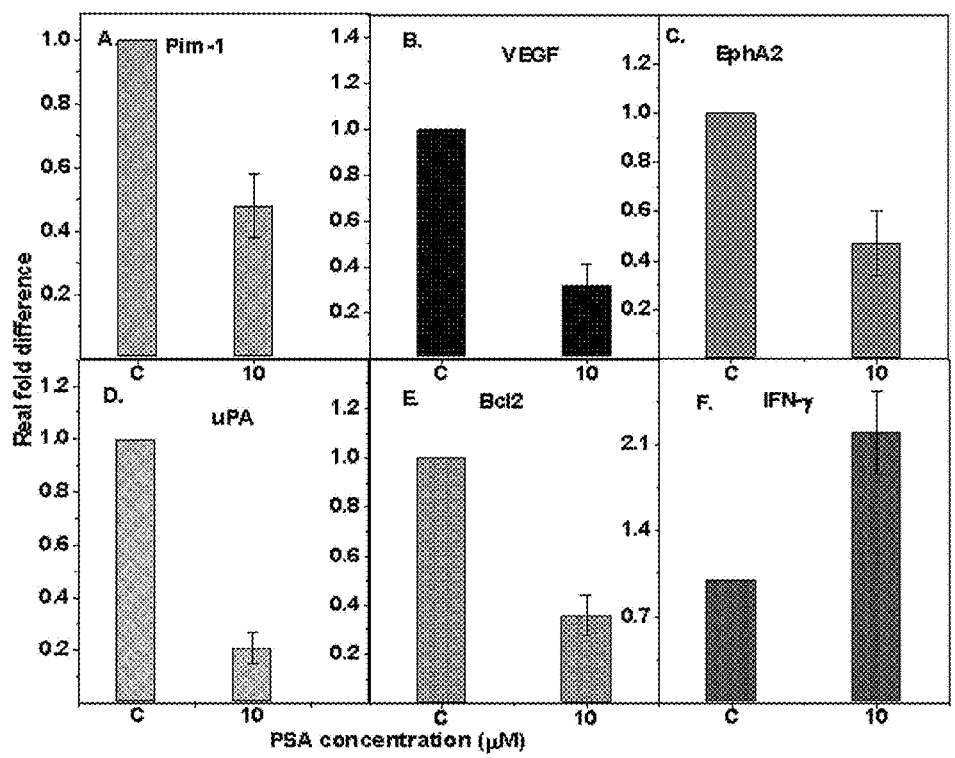
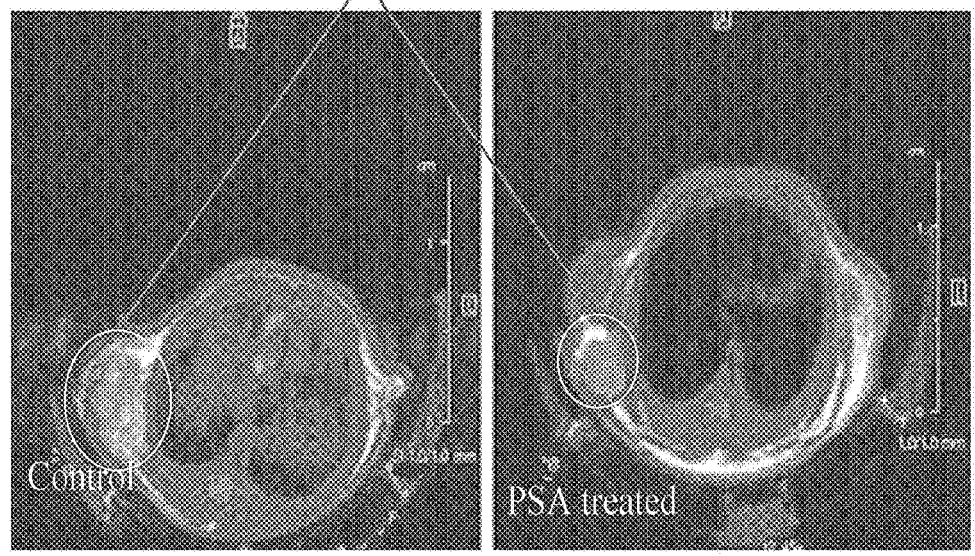

Comparison of the effect of SP and Tissue (NT) PSA in HUVEC In vitro Angiogenesis Assay 107-119   (peptide 1) lys,asn,arg,phe,leu,arg,pro,gly,asp,asp,ser,ser,his (13) (red) 2 SEQ ID NO:1)
156-172   (peptide 2) gly,trp,gly,ser,ile,glu,pro,glu,glu,phe,leu,thr,pro,lys,lys,leu,gln (17) (green) SEQ ID NO:2
181-194   (peptide 3) asn,asp,val,cys,ala,gln,val,his,pro,gln,lys,val,thr,lys (14) (blue) SEQ ID NO:3
200-210   (peptide 4) gly,arg,trp,thr,gly,gly,lys,ser,thr,cys,ser (11) (yellow) SEQ ID NO:4
231-241   (peptide 5) ser,glu,pro,cys,ala,leu,pro,glu,arg,pro,ser (11) (purple) SEQ ID NO:5

Figure 12

Mass Spectroscopy results

KLK3 (PSA) HUMAN

X linker
|
    Biotin
    |
K$^{251}$WIK$^{254}$DTIVANP
(SEQ ID NO:32)

Biotin
|
    Biotin
    |
K$^{251}$WIK$^{254}$DTIVANP
(SEQ ID NO:32)

*RSSA HUMAN

X linker     X linker
|          |
K$^{42}$SDGIYIINLK$^{52}$R
(SEQ ID NO:33)

X linker
|
TWEK$^{57}$LLLAAR
(SEQ ID NO:34)

X linker
|
AVLK$^{89}$FAAATGATPIAGR
(SEQ ID NO:36)

**ICAM2 HUMAN

X linker
|
QVILTLQPTLVAVGK$^{128}$SFTIECR
(SEQ ID NO:35)

*target molecule 1: 40S ribosomal protein SA (RPSA) or laminin receptor (LR)
**target molecule 2: intercellular adhesion molecule 2 (ICAM-2)
X linker: CAMthiopropanoyl
Biotin: NHS-LC-Biotin

US 10,034,913 B2

ANTI-ANGIOGENIC PEPTIDES AND USES THEREOF

CROSS-REFERENCE TO RELATED APPLICATIONS

This application is a divisional application of U.S. patent application Ser. No. 14/235,563, filed Jul. 3, 2014, which is a National Phase of International patent application no. PCT/US2012/047803, filed Jul. 23, 2012, which claims priority to U.S. provisional patent application No. 61/513,019, filed Jul. 29, 2011, the disclosures of each of which are incorporated herein by reference.

STATEMENT REGARDING FEDERALLY SPONSORED RESEARCH AND DEVELOPMENT

This invention was made with government support under CA077739 as awarded by the National Institutes of Health. The government has certain rights in the invention.

FIELD OF THE INVENTION

The present invention relates generally to cancer therapy and more specifically to novel peptides for use as anti-angiogenic/anti-cancer agents.

BACKGROUND OF THE INVENTION

Prostate cancer is a major contributor to cancer mortality in American males causing projected death of approximately 27,360 men in 2009 (Jemal et al., Cancer J. Clin., 59: 225-249, 2009). Therapeutic modaliPSAties such as radical prostatectomy and radiotherapy are sometimes curative for localized disease, yet no treatments for metastatic prostate cancer that significantly increases patient survival are available.

Angiogenesis is critical in tumor progression and metastasis in most if not all solid tumors, since a functional vascular supply is required for the continued growth of solid tumors and the spread of cancer cells. Small non-growing tumors may remain dormant for years and the angiogenic switch to aggressive metastatic phenotype involves a change in the local equilibrium between factors inducing blood vessel formation and those inhibiting the process.

There is an ongoing and unmet need to develop compositions and methods for inhibiting angiogenesis as a therapeutic modality for treating solid tumors, and in particular, for prophylaxis and/or therapy of prostate tumors. The present invention meets this need.

SUMMARY OF THE INVENTION

The present invention provides peptides and methods of using the peptides for inhibiting angiogenesis. Thus, the invention provides compositions and methods for use in therapeutic interventions for treating diseases that include but are not limited to cancer.

The peptides of the invention include but are not limited to peptides comprising or consisting of amino acid sequences disclosed herein, fragments of the amino acid sequences, and modifications of peptides comprising amino acid sequences derived from prostate specific antigen (PSA). Each peptide and peptide that can be modified as described herein and which is encompassed within the scope of the invention has the capability to inhibit human endothelial cell migration, such as endothelial cell migration in a gelatinous protein mixture, such as that sold under the name Matrigel. Thus, in one embodiment, a peptide encompassed within the scope of the invention is a peptide that can inhibit cell network formation in a gelatinous protein mixture.

In particular embodiments, the amino acids of the peptides provided by the invention comprise or consist of the following sequences:

Lys Asn Arg Phe Leu Arg Pro Gly Asp Asp Ser Ser His (SEQ ID NO:1). This peptide is also referred to herein as Peptide #1 (linear) and as "PSA-P1L." It is not provided as a cyclic peptide. A modified version of this peptide is provided and is referred to herein as PSA-P1C (constrained, or cyclized). It has the sequence Cys Lys Asn Arg Phe Leu Arg Pro Gly Asp Asp Ser Ser His Cys (SEQ ID NO:7). In this peptide, a cysteine was engineered at the N-terminus and at the C-terminus of Peptide #1. These facilitate formation of a disulfide bond between the N- and C-terminal cysteine residues. The result is a cyclic ("constrained" or cyclized) peptide wherein the N- and C-termini are connected to one another via a disulfide bond.

In another embodiment, Peptide #2 is provided. It has the sequence Gly Trp Gly Ser Ile Glu Pro Glu Glu Phe Leu Thr Pro Lys Lys Leu Gln (SEQ ID NO:2).

In another embodiment, Peptide #3 is provided. It has the sequence Asn Asp Val Cys Ala Gln Val His Pro Gln Lys Val Thr Lys (SEQ ID NO:3).

In another embodiment, Peptide #3 is modified to replace the Cys that is endogenous to PSA with Ala, to provide Peptide 3*. Peptide 3* has the sequence Asn Asp Val Ala Ala Gln Val His Pro Gln Lys Val Thr Lys (SEQ ID NO:8).

In another embodiment, Peptide #4 is provided. It has the sequence Gly Arg Trp Thr Gly Gly Lys Ser Thr Cys Ser (SEQ ID NO:4).

In another embodiment, Peptide #5 is provided. It has the sequence Ser Glu Pro Cys Ala Leu Pro Glu Arg Pro Ser (SEQ ID NO:5).

In another embodiment, Peptide #6 is provided. It has the sequence Asn Asp Val Cys Ala Gln Val His Pro Gln Lys Val Thr Lys Phe Met Leu Cys Ala (SEQ ID NO:6). Peptide #6 is also referred to herein as "PSA-P3C". The two Cys in PSA-P3C can cyclize (constrain) the peptide via a disulfide bond. In one embodiment, Peptide #6 is modified so that the two Cys residues in it are replaced by Ala to provide a peptide which has the sequence Asn Asp Val Ala Ala Gln Val His Pro Gln Lys Val Thr Lys Phe Met Leu Ala Ala (SEQ ID NO:9). This peptide is referred to herein as "PSA-P3L" and is not provided in cyclic form.

The method comprises administering a composition comprising one or more peptides comprising or consisting of an amino acid sequence as described herein to an individual in an amount effective to inhibit angiogenesis, and/or in an amount effective to inhibit the growth and/or metastasis of a tumor. Other diseases that involve undesirable or irregular angiogenesis are also contemplated for treatment. Compositions comprising the peptides are also provided. Such compositions include but are not necessarily limited to pharmaceutical preparations.

BRIEF DESCRIPTION OF THE FIGURES

FIG. 1 top, is a graphical depiction of PSA-induced alteration of expression of select genes in PC-3M cells. The affected genes in the panels in FIG. 1 top are: Panel A (Pim-1), Panel B (VEGF), Panel C (EphA2), Panel D (uPA), Panel E (Bcl2), Panel F (IFN-γ). FIG. 1, bottom, is a representation of a functional-Magnetic Resonance Image (f-MRI) analysis of PSA-induced inhibition of growth of PC-3M xenografts.

FIG. 12 depicts mass spectroscopy analysis of selected proteins and suggests that by identifying cell membrane proteins that bind to PSA by co-precipitation, it will be possible to identify the receptor for PSA that transmits the signal into the cell that changes gene transcription and angiogenic activity. The data were obtained by treatment of HUVEC with biotinylated-PSA at 4 C to identify the ligand(s) that may be the part of receptor. Two targets were identified: 40S ribosomal protein SA and intracellular adhesion molecule 2 (ICAM-2).

DESCRIPTION OF THE INVENTION

Figure 2:
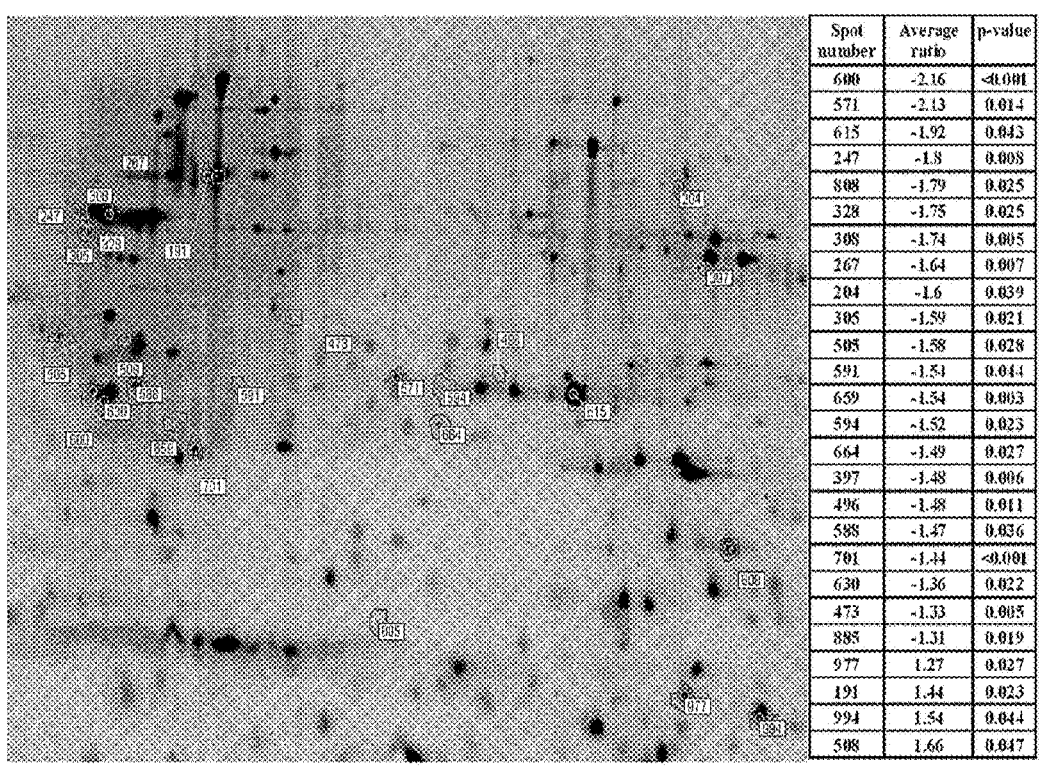
FIG. 2 is a photographic representation and table showing PSA-mediated protein modulation in PC-3M cells as determined by 2-dimensional difference gel electrophoresis (2D-DIGE) analysis.

The present invention provides isolated peptides derived from PSA that are expected to be capable of inhibiting angiogenesis in vivo, compositions comprising the peptides, and methods of using the peptides to inhibit angiogenesis.

In more detail, PSA (also referred to in the art as KLK3) is widely recognized by the lay population as the serum biomarker utilized for screening for the presence, aggressiveness and/or recurrence of prostate cancer. However, recent observations have called into question the utility of PSA as a screening or diagnostic tool, and the biology of PSA production and function in the human prostate is not consistent with a causal role for PSA in the progression of prostate cancer. PSA is at $10^6$-fold greater levels in seminal fluid, and $10^3$-fold greater levels in the prostate tissue, than the level of PSA present in the serum of post-pubertal males. The PSA in seminal fluid and prostate tissue is largely enzymatically active and is not complexed with chaperone/carrier proteins, whereas, PSA in serum is largely enzymatically inactive and sequestered through binding to chaperone/carrier proteins. Furthermore, prostate production of PSA falls with age, prostate cancer progression and androgen deprivation therapy, whereas, the serum levels of PSA measured in the screening test rise even though prostate production of PSA is falling.

PSA was cloned and characterized as a product of the human prostate gland, however, PSA is produced by many organs in the human, in both males and females. In females, PSA is produced in benign breast, endometrial and ovarian tissues, and malignancies of these tissues, as well as in non-hormonally regulated tissues and their cancers, such as the parotid gland. Across all of these malignancies, including prostate cancer, tissue levels of PSA in the cancer tissue are inversely correlated with prognosis.

PSA is well known to undergo proteolytic processing from a full length protein that initially contains a signal peptide sequence (residues 1-17 of the full length protein), a sequence corresponding to an activation peptide (residues 18-24), and the processed PSA protein, which ordinarily consists of 237 amino acids spanning residues 25-261 of the full length protein. The 237 amino acid protein (25-261) were used in the studies that include PSA as described herein. The full length (i.e., unprocessed) protein consists of the amino acid sequence:

(SEQ ID NO: 10)
MWVPVVFLTLSVTWIGAAPLILSRIVGGWECEKHSQPWQVLVASRGRAVC

GGVLVHPQWVLTAAHCIRNKSVILLGRHSLFHPEDTGQVFQVSHSFPHPL

-continued
YDMSLLKNRFLRPGDDSSHDLMLLRLSEPAELTDAVKVMDLPTQEPALGT

TCYASGWGSIEPEEFLTPKKLQCVDLHVISNDVCAQVHPQKVTKFMLCAG

RWTGGKSTCSGDSGGPLVCNGVLQGITSWGSEPCALPERPSLYTKVVHYR

KWIKDTIVANP.

The principal biological function of PSA is currently believed to be in liquification of seminal fluid. PSA has also been shown to have significant transcriptional regulatory activity, modulating expression of multiple potent anti-angiogenic genes and processes. The present invention provides evidence that the transcriptional regulatory, anti-tumorigenic, and anti-angiogenic activity of human PSA are independent of the enzymatic activity of PSA, in that these biological endpoints are observed at equal molar concentrations of enzymatically inactive PSA. We demonstrate using established techniques for evaluating anti-angiogenic agents that the anti-angiogenic activity is exhibited by small peptides that we have derived from human PSA. Thus, the present invention provides a plurality of peptides derived from PSA, each of which is expected to be useful for inhibition of angiogenesis, either alone, or in combination with each other. Each peptide and derivative(s) thereof that are encompassed within the scope of the present invention has the capability to inhibit human endothelial cell migration in a gelatinous protein mixture. Thus, the invention provides a method of inhibiting human endothelial cell migration comprising contacting human endothelial cells with a composition comprising a peptide described herein, wherein the migration is inhibited subsequent to the contacting of the human endothelial cells with the composition. Also provided is a method of inhibiting angiogenesis and/or tumor growth and/or metastasis. The method comprises administering a composition comprising one or more of the peptides of the invention to an individual in an amount effective to inhibit angiogenesis, and/or inhibit tumor growth and/or inhibit metastasis. Also provided pharmaceutical preparations comprising the peptides, which can be used in the methods of the invention.

Without intending to be bound by any particular theory, it is considered that PSA is an endogenous anti-neoplastic factor in many human tissues and their malignancies, and that the peptides described herein will provide anti-angiogenic activity targeted to the immature/angiogenic tumor vascular network, thus inhibiting angiogenesis, and/or tumor progression and/or metastasis. The peptides described herein are believed to represent ideal therapeutic modalities in that they are a derived from a constitutively expressed protein that should not elicit an immune response, and systemic administration is expected to provide direct delivery to the therapeutic target, namely, the endothelial cells of the cancer.

Data presented herein show that a subset of synthetic peptides derived from human PSA inhibit angiogenesis in the Matrigel endothelial cell tube formation assay. It is noteworthy that tube formation in Matrigel by cultured endothelial cells, usually HUVEC, is an established in vitro surrogate for angiogenesis that is proposed to require both migration and differentiation by the endothelial cells. The "tube formation" assay has been utilized extensively to evaluate in vitro the anti-angiogenic capacity of peptides, proteins and pharmacologic agents (Print, C., et al., Soluble factors from human endometrium promote angiogenesis and regulate the endothelial cell transcriptome. Hum Reprod, 2004. 19(10): p. 2356-66; Delves, G. H., et al., In vitro inhibition of angiogenesis by prostasomes. 2005. Prostate Cancer Prostatic Dis. 8(2): p. 174-8). Thus, results presented herein are strongly indicative that the peptides of the invention will be suitable for inhibition of angiogenesis, and thus can be expected to be useful for prophylaxis and/or therapy of human cancers, including but not limited to prostate cancer, breast cancer, ovarian cancer, cervical cancer and parotid cancers. In certain embodiments, the invention provides a method for inhibiting the migration and/or differentiation of human endothelial cells comprising contacting the cells with a composition comprising one or more peptides of the invention.

TABLE 1

PSA levels in paired tumor and non-tumor tissue

| Donor | Tumor tissue [ng PSA/ug DNA] | Non-tumor tissue [ng PSA/ug DNA] |
|---|---|---|
| 1. | 1759 | 2118 |
| 2. | 918 | 2270 |
| 3. | 1027 | 1796 |
| 4. | 359 | 777 |
| 5. | 303 | 1435 |
| 6. | 504 | 1856 |
| 7. | 815 | 2017 |
| 8. | 1023 | 2491 |
| 9. | 1159 | 1408 |
| 10. | 1333 | 1921 |
| 11. | 224 | 879 |
| 12. | 414 | 862 |
| 13. | 440 | 1660 |
| 14. | 659 | 1440 |
| 15. | 448 | 1095 |
| Average | 759 | 1601 |

The data in Table #1 shows that PSA levels in prostate gland as expressed in prostate cancer tissue are lower than in benign tissue in the same gland. At the time of surgery, prostate tissue, that is removed, is checked by pathology to determine what portion of tissue is benign and what portion is malignant. Thus, Table 1 establishes that tissue PSA is down regulated in cancerous tissue. The significance of the data presented in this Table, without intending to be bound by any particular theory, is that since it is generally accepted that serum PSA levels increase in prostate cancer, it is not a logical hypothesis that PSA is an endogenous antiangiogenic factor. However, we have determined that malignant tissues actually make less PSA than normal tissue (as described in the Table) which actually reduces expression of the endogenous antiangiogenic agent.

The following peptide sequences illustrate embodiments of peptides encompassed by the present disclosure. It is notable that Peptides #2, #4 and #5 did not demonstrate reproducible anti-angiogenic activity. Thus, not all fragments of PSA exhibit anti-angiogenic properties.

Lys Asn Arg Phe Leu Arg Pro Gly Asp Asp Ser Ser His (SEQ ID NO:1). This peptide is also referred to in the description of the invention and the Examples as Peptide #1 and as "PSA-P1L." This peptide is not cyclized. We modified this peptide to provide the peptide referred to herein as "PSA-P1C." It has the sequence Cys Lys Asn Arg Phe Leu Arg Pro Gly Asp Asp Ser Ser His Cys (SEQ ID NO:7). To derive PSA-P1C, we engineered a cysteine at the N-terminus and at the C-terminus of Peptide #1, which enabled formation of a disulfide between the N- and C-terminal residues. The result is a cyclic peptide wherein the N- and C-termini are connected to one another via a disulfide bond. In all cases where PSA-P1L is tested in the data presented herein it was tested in the cyclic form.

Peptide #2 is provided and has the sequence Gly Trp Gly Ser Ile Glu Pro Glu Glu Phe Leu Thr Pro Lys Lys Leu Gln (SEQ ID NO:2).

In another embodiment, Peptide #3 is provided and has the sequence Asn Asp Val Cys Ala Gln Val His Pro Gln Lys Val Thr Lys (SEQ ID NO:3).

We modified Peptide #3 to replace the Cys that is endogenous to PSA with Ala, resulting in Peptide 3*. Peptide 3* has the sequence Asn Asp Val Ala Ala Gln Val His Pro Gln Lys Val Thr Lys (SEQ ID NO:8).

Peptide #4 has the sequence Gly Arg Trp Thr Gly Gly Lys Ser Thr Cys Ser (SEQ ID NO:4). Peptide #5 has the sequence Ser Glu Pro Cys Ala Leu Pro Glu Arg Pro Ser (SEQ ID NO:5).

In another embodiment, Peptide #6 is provided. It has the sequence Asn Asp Val Cys Ala Gln Val His Pro Gln Lys Val Thr Lys Phe Met Leu Cys Ala (SEQ ID NO:6). Peptide #6 is also referred to herein as "PSA-P3C." The two Cys in PSA-P3C are used to cyclize the peptide via a disulfide bond. PSA-P3C was tested in the experiments described herein in cyclic form. We modified Peptide #6 to test a similar peptide in linear form. To do this, the two Cys residues in Peptide #6 were replaced by Ala to provide a peptide which has the sequence Asn Asp Val Ala Ala Gln Val His Pro Gln Lys Val Thr Lys Phe Met Leu Ala Ala (SEQ ID NO:9). This peptide is referred to herein as "PSA-P3L".

It is expected that the amino acids sequences of the peptides presented herein and described as suitable for use in the invention can be modified and still retain desirable properties, such as anti-angiogenic properties. Such modifications can be determined in a variety of ways, such as by almandine scanning mutagenesis. Illustrative, non-limiting examples of peptide derivatives based upon Peptide #1 that can be produced in this manner, and are therefore included within the scope of the invention, are illustrated by the following sequences:

```
                                        (SEQ ID NO: 11)
lys ala arg phe leu arg pro gly asp asp ser ser his (SEQ ID NO: 12)
lys asn ala phe leu arg pro gly asp asp ser ser his (SEQ ID NO: 13)
lys asn arg ala leu arg pro gly asp asp ser ser his (SEQ ID NO: 14)
lys asn arg phe ala arg pro gly asp asp ser ser his (SEQ ID NO: 15)
lys asn arg phe leu ala pro gly asp asp ser ser his (SEQ ID NO: 16)
lys asn arg phe leu arg ala gly asp asp ser ser his (SEQ ID NO: 17)
lys asn arg phe leu arg pro ala asp asp ser ser his (SEQ ID NO: 18)
lys asn arg phe leu arg pro gly ala asp ser ser his (SEQ ID NO: 19)
lys asn arg phe leu arg pro gly asp ala ser ser his (SEQ ID NO: 20)
lys asn arg phe leu arg pro gly asp asp ala ser his SEQ ID NO: 21)
lys asn arg phe leu arg pro gly asp asp ser ala his (SEQ ID NO: 22)
lys asn arg phe leu arg pro gly asp asp ser ser ala
```

The invention includes peptides of various lengths, and with various amino acid substitutions, based on the amino acid sequences of the peptides provided by the invention. For example, Peptide #1 (or any other peptide described herein) can be modified by conservative amino acid substitutions that are based generally on relative similarity of R-group substituents. Non-limiting examples of such substitutions contemplated in the present invention include, but are not limited to: gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, peptides that comprise any single conservative amino acid substitution, or any combination of conservative amino acid substitutions, are included in the invention, so long as they retain their anti-angiogenic properties. In certain embodiments, peptides of the invention which comprise conservative amino acid substitutions retain their capability to inhibit tubule formation by HUVECs.

Non-conservative substitutions that enhance desirable characteristics of the peptides, such as their anti-angiogenic activity, circulation time, bioavailability, stability, binding to cell surface receptors, regulation of gene transcription, targeting imaging or therapeutic modalities to the tumor vasculature, etc., are also included in the invention.

In addition to amino acid substitutions, peptides of the invention may include fragments of any of the peptides described herein. Any peptide encompassed within the scope of the invention can comprise or consist of from 4-20 amino acids, inclusive, and including all integers there between. For example, Peptide #1 fragments encompassed within the scope of the invention include but are not limited to:

```
                                          (SEQ ID NO: 23)
asn-arg-phe-leu-arg-pro-gly-asp-asp-ser-ser-his (SEQ ID NO: 24)
    arg-phe-leu-arg-pro-gly-asp-asp-ser-ser-his (SEQ ID NO: 25)
        phe-leu-arg-pro-gly-asp-asp-ser-ser-his (SEQ ID NO: 26)
            leu-arg-pro-gly-asp-asp-ser-ser-his (SEQ ID NO: 27)
                arg-pro-gly-asp-asp-ser-ser-his (SEQ ID NO: 28)
                    pro-gly-asp-asp-ser-ser-his (SEQ ID NO: 29)
                        gly-asp-asp-ser-ser-his (SEQ ID NO: 30)
                            asp-asp-ser-ser-his (SEQ ID NO: 31)
                                asp-ser-ser-his
```

Each peptide described herein can also be truncated by any number of amino acids at its C-terminus, and by any number of amino acids at both the N- and C-termini, so long as the remaining sequence retains its anti-angiogenic activity. Each of the foregoing fragments can also be subjected to the aforementioned amino acid substitutions, and thus, fragments having such substitutions are included within the scope of the invention. Any peptide provided by the invention can comprise one, two, three, four, or five conservative amino acid substitutions. Any of the peptides provided by the invention can be at least four amino acids in length.

To the extent that any of the peptides/fragment sequences per se have been previously described, then the present invention contemplates their use in methods for inhibition of angiogenesis, and/or for the prophylaxis and/or treatment of tumors and/or metastasis, and in pharmaceutical preparations. It is also contemplated that the peptides of the present invention may include additional amino acids, and may include modified amino acids that can improve any desirable property of the peptides. Thus, the peptides could be covalently or non-covalently associated with any desirable moiety that would be expected to improve their functional capabilities in accordance with the method of the invention.

The peptides of the invention can be prepared by any technique known to those skilled in the art or by techniques hereafter developed. For example, the peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). The synthesis of peptides by solution methods may also be used, as described in The Proteins, Vol. II, 3d Ed., p. 105-237, Neurath, H., et al., Eds., Academic Press, New York, N.Y. (1976). The synthesized peptides may be substantially purified by preparative high performance liquid chromatography or other comparable techniques available in the art. The composition of the synthetic peptides can be confirmed by an technique for amino acid composition analysis.

In one embodiment, the peptides are provided as cyclic peptides.

For use in angiogenesis inhibition, prophylaxis and/or therapy of tumors and/or metastasis, the peptides can be administered in a conventional dosage form prepared by combining the peptides with a standard pharmaceutically acceptable carrier according to known techniques. Some examples of pharmaceutically acceptable carriers can be found in: *Remington: The Science and Practice of Pharmacy* (2005) 21st Edition, Philadelphia, Pa. Lippincott Williams & Wilkins.

In one embodiment, the invention comprises at least one of the peptides provided by the invention in a pharmaceutical preparation, such as a composition comprising at least one pharmaceutically acceptable carrier, which can be provided in a pharmaceutically acceptable buffer. In certain embodiments, compositions of the invention can include distinct peptides, and can include mixtures of linear (non-cyclic) and cyclic peptides.

Various methods known to those skilled in the art may be used to introduce the compositions of the invention to an individual. These methods include but are not limited to intracranial, intrathecal, intradermal, intramuscular, intraperitoneal, intravenous, subcutaneous, oral, intranasal and retrograde routes.

It will be recognized by those of skill in the art that the form and character of the particular dosing regime employed in the method of the invention will be dictated by the route of administration and other well-known variables, such as rate of clearance, the size of the individual and the stage of the particular disease being treated. Based on such criteria, one skilled in the art can determine an amount of any of the particular peptides described herein that will be effective to inhibit angiogenesis and/or tumor growth for any particular individual. It is generally considered that the amount of peptide administered will range from microgram to milligram amounts.

The method of the invention can be performed in conjunction with conventional anti-cancer therapies. Such therapies can include but are not limited to chemotherapies, such as androgen deprivation therapy, surgical interventions, and radiation therapy. The compositions of the invention could be administered prior to, concurrently, or subsequent to such anti-cancer therapies.

The following Examples are meant to illustrate, but not limit the invention.

Example 1

This Example demonstrates PSA-induced inhibition of gene expression in human prostate cancer cells.

The human prostate cancer cell lines LNCaP, DU-145 and PC-3 have low, moderate and high metastatic potential, and we reported that expression of pro-angiogenic factors correlated with the metastatic potential (Aalinkeel R, et al., 2004. Cancer Res 64:5311-5321). Constitutive expression of multiple pro-angiogenic growth factors, including: VEGF, IL-8 and TGF-β, as well as MMP-9 and tissue inhibitors of metalloproteinase 1 and 4, was significantly greater in the highly metastatic PC-3M cell line compared to LNCaP cells, with a low intrinsic metastatic potential (Aalinkeel R, et al., 2004. Cancer Res 64:5311-5321).

PSA purified to homogeneity from human seminal plasma is enzymatically active, and free of contaminating hk2, and complexes with carrier proteins/chaperones (Bindukumar, B., et al., J Chromatogr B Analyt Technol Biomed Life Sci, 2004. 813(1-2): p. 113-20). Gene expression array analysis of PC-3M cells versus LNCaP cells treated with 10 μM PSA, revealed that 136 genes were up-regulated and 137 genes were down-regulated. QPCR analysis demonstrated that urokinase-type plasminogen activator (uPA), VEGF, cysteine-rich angiogenic inducer-61, EphA2, TGF-β2. were significantly down-regulated in the highly metastatic PC-3M cells, whereas, IFN-γ and several interferon related genes, including 2,5 oligo-adenylated synthetase-2, were up-regulated (FIG. 1, top). The effect of PSA on VEGF and IFN-γ gene expression and protein release in PC-3M cells was distinctly dose dependent (Bindukumar, B., et al., Neoplasia, 2005. 7(3): p. 241-52). Consistent with the down-regulation of genes that stimulate tumor growth and induce angiogenesis in vitro summarized in FIG. 1, top, we demonstrated that PSA inhibited growth of PC-3M xenografts in nude mice (FIG. 1, bottom, mean tumor volume 13 mm$^3$ when PSA was administered in the tumor vicinity, compared to mean tumor volume in control animals, 267 mm$^3$] (Bindukumar, B., et al., Neoplasia, 2005. 7(3): p. 241-52).

Example 2

Figure 3:
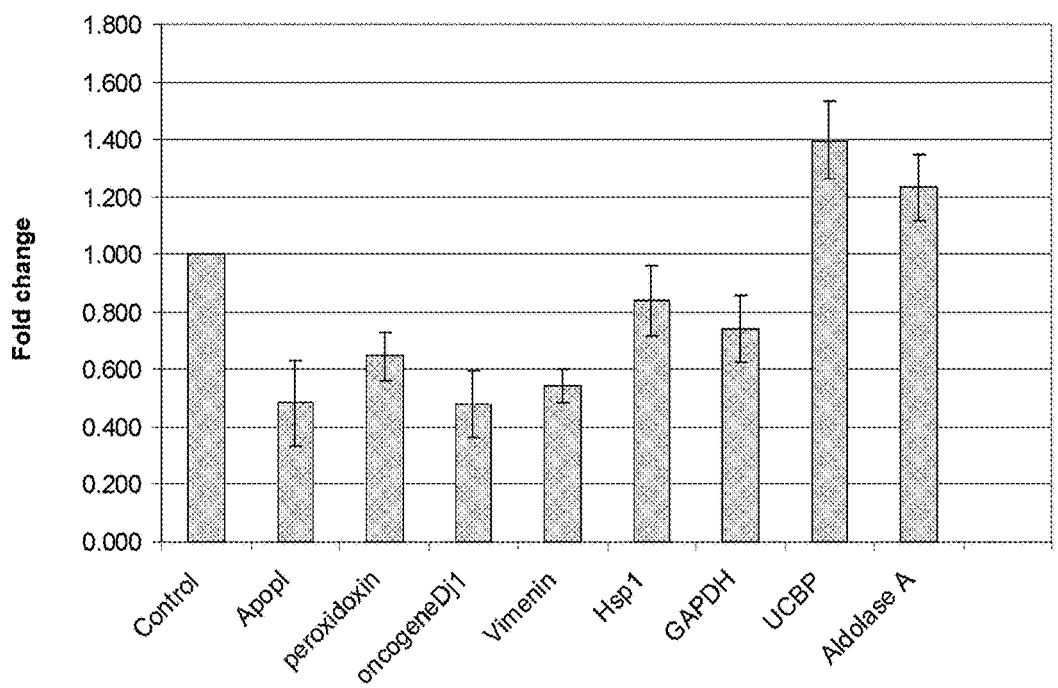
FIG. 3 is a graphical representation of data obtained from quantitative real time polymerase chain reaction (Q-PCR) analysis of PSA-mediated modulation of gene expression in Human umbilical vein endothelial (HUVEC) treated with 10 μM PSA using Peptide No. 3.

This Example provides an illustration of proteomic profiling of the effect of PSA on human prostate cancer cells. In this regard, a proteomic approach was employed to identify proteins whose expression was modulated in PC-3M cells treated with PSA. 2D-DIGE coupled with HPLC-tandem mass spectrometry (MS/MS) identified a total of 41 proteins significantly changed (p<0.05) in abundance in PC-3M cells in response to PSA treatment. Proteins from 26 gel spots were identified [FIG. 2]. Many of down-regulated proteins, including: the N8 gene product long isoform, laminin receptor, vimentin, DJ-1 and Hsp60, are known to be involved in tumor progression. Specificity of PSA modulation of differential expression of these genes in PC-3M cells was validated at the gene level by RT-QPCR [FIG. 3].

Example 3

This Example demonstrates enzymatic activity of isolated PSA. In particular, enzymatic activity of PSA isolated from human seminal plasma (f-PSA) and from human prostate cancer tissue specimens (Tissue-PSA: T-PSA) was evaluated routinely using a substrate (Mu-His-Ser-Ser-Lys-Leu-Gln—AFC) (SEQ ID NO:102) (Calbiochem) that is highly specific for PSA. In connection with the human prostate cancer tissue specimens, it should be noted that the majority of PSA in serum is complexed with serine protease inhibitors and is enzymatically inactive, while essentially all of the PSA in seminal fluid is in a free form (f-PSA) and is enzymatically active. PSA in the tissue microenvironment (T-PSA) is largely free and enzymatically active. T-PSA levels are lower in advanced prostate cancer than benign prostate, and T-PSA levels correlate with prognosis in prostate cancer, as well as in breast cancer; the higher the T-PSA level, the better the prognosis.

Hydrolysis of the fluorogenic substrate was quantitated using a LS-45 Luminescence Spectrometer from Perkin Elmer) using the FL-Winlab® program. Human prostate cancer tissue specimens were obtained from the Pathology Resource Network at Roswell Park Cancer Institute under an IRB approved protocol. Both f-PSA and T-PSA demonstrated enzymatic activity in the assay, however, T-PSA routinely demonstrated roughly 50% of the activity of f-PSA from seminal plasma per microgram of protein, probably reflecting loss of activity during extraction from tissue. Enzymatic activity against the fluorescent substrate of both f-PSA and T-PSA were inhibited completely by pre-incubation with zinc chloride (5 µM).

Example 4

This Example demonstrates that enzymatic activity of PSA is not required for its effects on modulating angiogenesis related gene expression.

Figure 4:
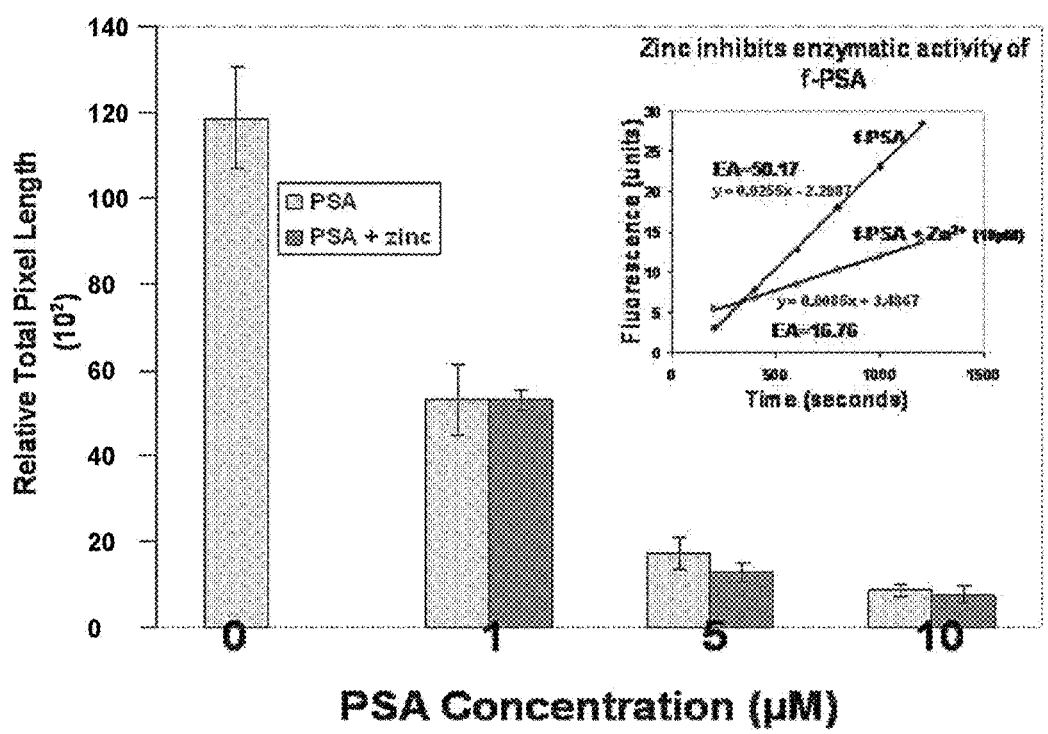
FIG. 4 is a graphical representation of data demonstrating that enzymatic activity of purified PSA (f-PSA) is not required for in vitro anti-angiogenic activity.
Figure 5:
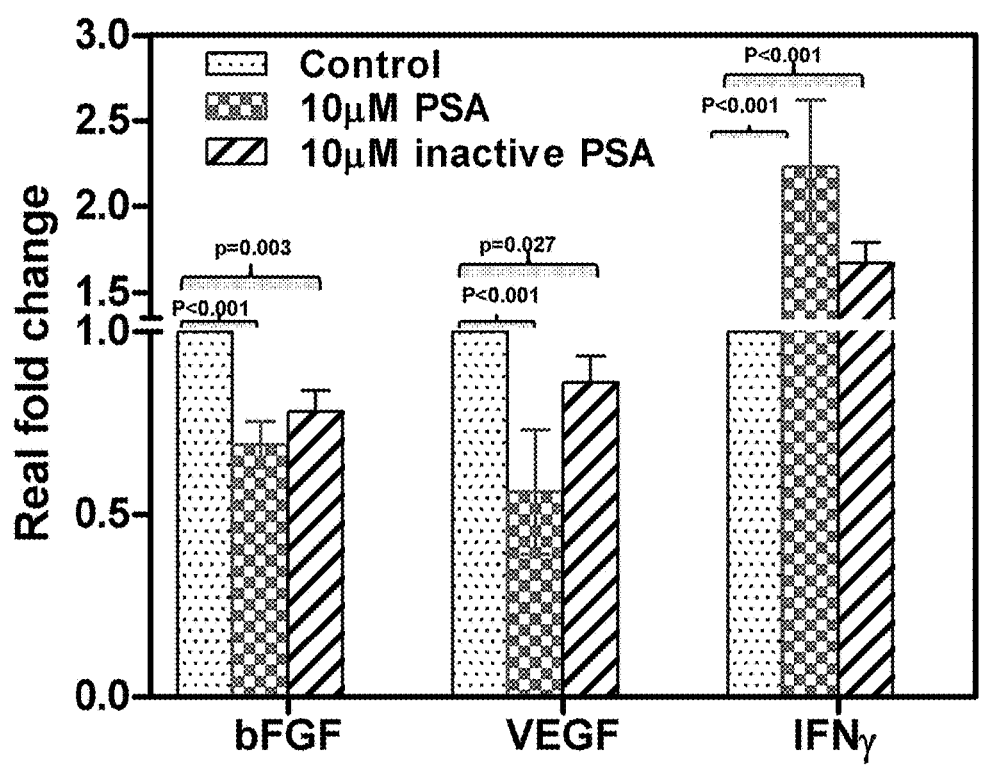
FIG. 5 is a graphical representation of data demonstrating effects of enzymatically active and enzymatically inactive f-PSA on gene expression in HUVEC cells.
Figure 6:
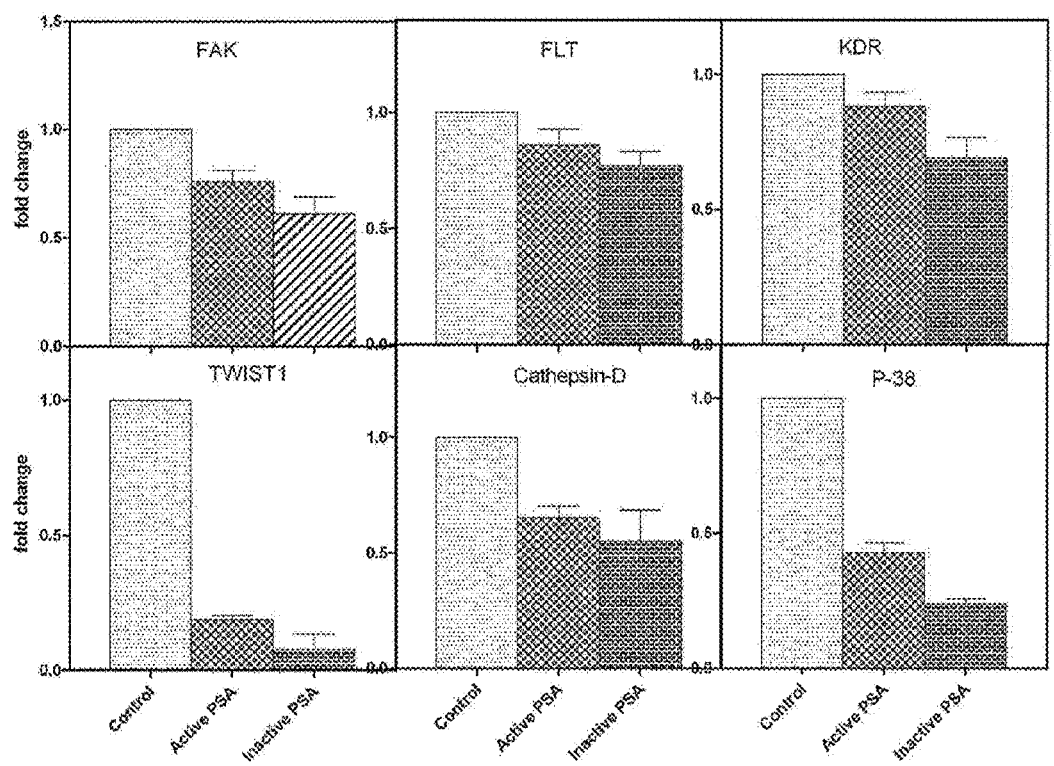
FIG. 6 is a graphical representation of data demonstrating effects of enzymatically active and enzymatically inactive f-PSA on expression of genes involved in angiogenesis in HUVEC.

Enzymatically active PSA, and PSA inactivated by incubation with $Zinc^{2+}$ [activity inhibited>75% by 5.0 µM of Zinc, inset FIG. 4] were compared for their respective effects on expression of genes involved in angiogenesis/vasculogenesis in HUVEC cells. FIG. 5 demonstrates that enzymatically active and inactive PSA were equally effective in negatively modulating expression of pro-angiogenic growth factors, including: bFGF and VEGF, as well as positively modulating expression of IFN-γ, in HUVEC cells (FIG. 5), and expression of genes involved in blood vessel development such as FAK, FLT, KDR, TWIST1, Cathepsin D and P-38 in HUVEC cells (FIG. 6).

Example 5

This Example demonstrates the effect of enzymatically active f-PSA and T-PSA on endothelial tube formation in the Matrigel Assay.

Figure 7:
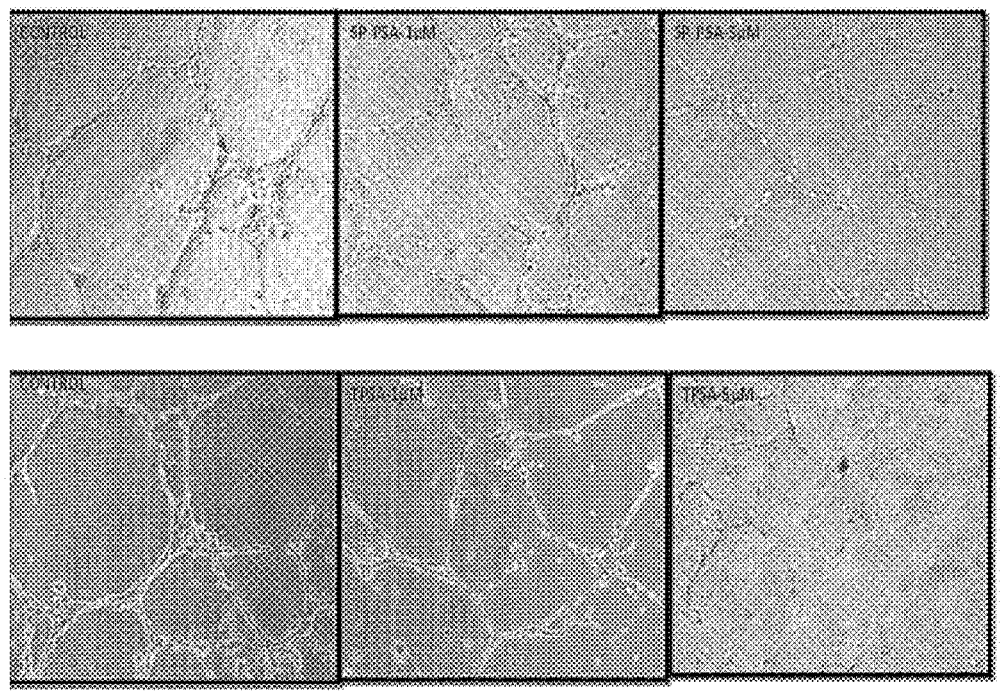
FIG. 7 is a photographic representation of Matrigel Endothelial Tube Formation Assay. NT=non-tumor tissue and SP=seminal plasma. Both types are intact and enzymatically active.

FIG. 7 demonstrates the anti-angiogenic activity of PSA in the Matrigel Endothelial Tube Formation Assay. Equimolar concentrations of both f-PSA and T-PSA demonstrated equivalent inhibitory activity in this in vitro assay of anti-angiogenic activity. Significantly, as demonstrated in the bar chart portion of FIG. 4, inhibition of endothelial tube formation by f-PSA was not dependent on enzymatic activity. Over the entire range of PSA concentrations studied, PSA inactivated by incubation with $Zn^{2+}$ was as inhibitory of tube formation as was native PSA (data not shown in this figure).

Example 6

Figure 8:
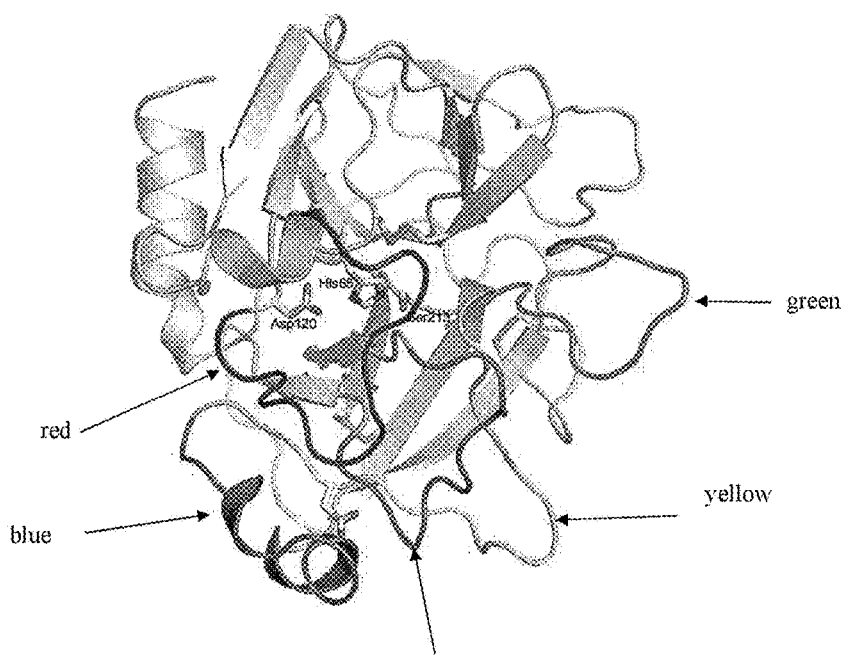
FIG. 8 is 3-Dimensional model of human PSA and depicts the location of five hydrophilic peptide sequences tested as described herein for anti-angiogenic activity.
Figure 9:
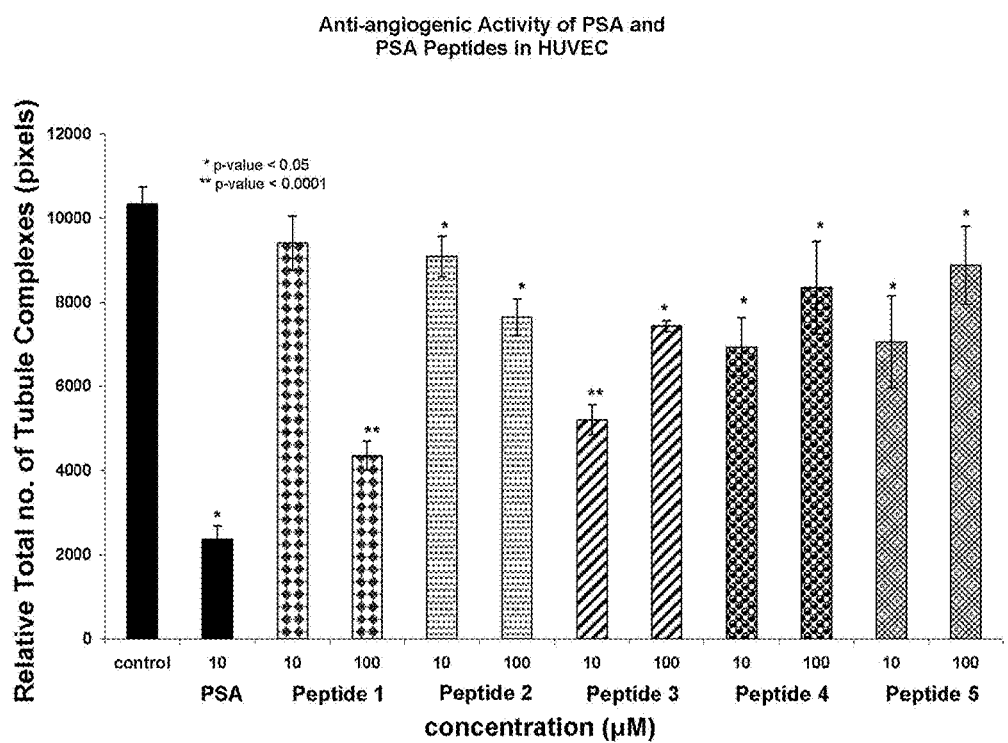
FIG. 9 is a graphical representation of data showing anti-angiogenic activity of five candidate PSA-mimetic peptides in the HUVEC tube formation assay. (Peptide 3 is asn-asp-val-ala-ala-gln-val-his-pro-gln-lys-val-thr-lys (SEQ ID NO: 8)).
Figure 10:
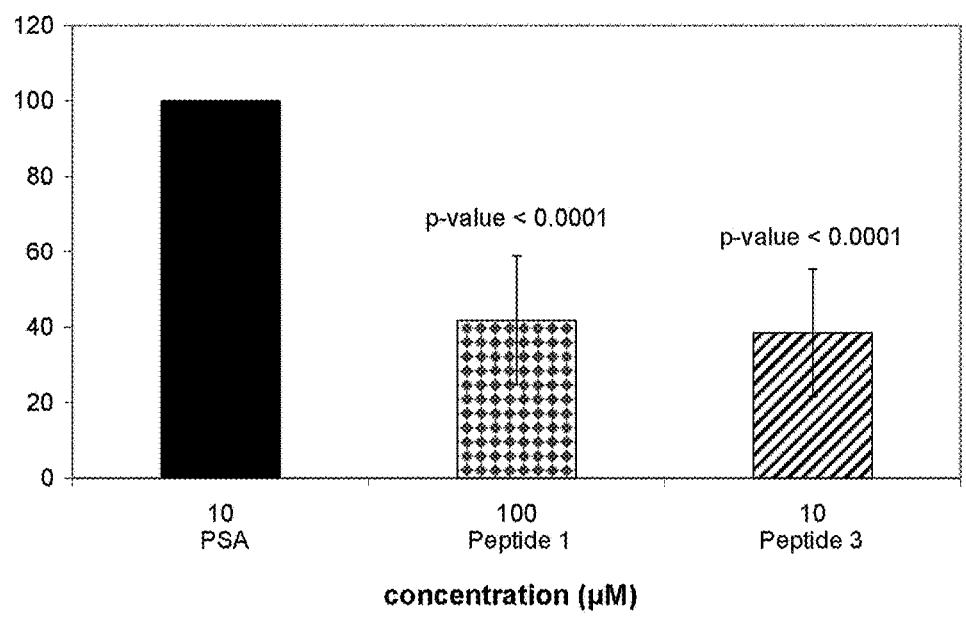
FIG. 10 is a graphical representation of data showing anti-angiogenic activity of Peptides 1 (SEQ ID NO:1) and 3*(SEQ ID NO:8) relative to the anti-angiogenic activity of native PSA.

This Example demonstrates that illustrative PSA-mimetic peptides provided by the invention have inhibitory effect upon endothelial tube formation by HUVEC in the Matrigel Assay. The 3-D model of human PSA, the amino acid sequence of the initial five candidate peptides, and their color-coded location on the exterior of the PSA protein molecule in aqueous solution, are presented in FIG. 8. Five PSA-mimetic peptides with >90% purity were acquired from GeneScript Corporation, Piscataway, N.J., and tested for anti-angiogenic activity against HUVECs in the Matrigel tube formation assay with intact PSA as the control (FIGS. 9 & 10). Briefly, to perform these assays, $10^4$ HUVEC cells are mixed with the PSA mimetic peptide, and, the mixture placed on top of a solidified, pre-poured Matrigel layer in a flat bottomed well of a multi-chambered plate, and the culture incubated for 16-18 hr to allow time for the endothelial cells to migrate and form tubular structures. At the conclusion of the incubation, digital images were made from the center of each culture to avoid bias, and 3-4 wells for each test condition were imaged. The images are processed under the Analyze 7.0 and "Angioquant" software packages, for imaging and quantification. The total length of tubular structures in the image is determined, and averaged over the replicate cultures. This method of quantification allows for accurate, unbiased measurement of tube lengths. Peptides having each of the peptide sequences shown in FIG. 8 are encompassed within the scope of the invention, including all modifications and substitutions to the sequences as described supra. Likewise, all methods of the invention described herein pertain to the peptide sequences shown in FIG. 8.

FIG. 9 shows the dose-related effect on angiogenesis (endothelial tube formation in Matrigel) (average of 5 individual determinations per experiment) for the five synthetic, PSA-mimetic peptides, at two different concentrations (10 and 100 µM), and enzymatically active native PSA (10 µM) as a positive control. The experimental endpoint, measured by digital image analysis, is the total area of the image comprised of endothelial cells (tubes). Analysis of total length of tubular structures, as well as area covered by tubular structures, produced comparable findings. The maximal inhibition of tubule formation was seen with Peptide #1 (amino acids 107-119 of PSA) at a concentration of 100 µM, and peptide #3 (PSA amino acids 181-194) at a concentration of 10 µM. While the reason for the decrease in the amount of anti-angiogenic activity in this figure when the concentration of the peptides is increased from 10 to 100 µM is not clear, it may be related to a dosing response observed in this case. As noted above, Peptides #2, #4 and #5 did not demonstrate reproducible anti-angiogenic activity, demonstrating that the peptides of the invention were not obvious design choices. FIG. 10 presents the evaluation of anti-angiogenic activity for peptides #1 and #3 relative to the level of inhibition by native PSA, averaged over multiple experiments with different parental populations of HUVEC cells. Across multiple sets of experiments, both peptides inhibited the angiogenic activity of HUVEC by 35-40% relative to native PSA.

Example 7

The stability of a peptide against proteolytic degradation is an important factor for the use of peptides in vivo. Peptides are frequently modified to prevent enzymatic degradation. Several approaches have been used to achieve peptide stability including use of D-amino acids, peptidomimetics or cyclization. For this Example we prepared a cyclic variant of peptide #3 and compared the biological activities of the linear and cyclic peptide. Peptide #3 ($^{181}$Asn Asp Val Cys Ala Gln Val His Pro Gln Lys Val Thr Lys) (SEQ ID NO:3) had one cysteine residue (#184) in its structure and it was replaced with alanine during synthesis. It is demonstrated that linear peptide #3 at 10 µM concentration significantly inhibits HUVEC tube formation in Matrigel (FIGS. 9 & 10). The single Cys in Peptide #3 was replaced to avoid potential disulfide formation with distinct proteins or peptides. Peptide #6 has essentially the same sequence as Peptide #3 with two exceptions. The sequence was extended to include five additional amino acid residues towards the carboxyl end in order to include another naturally existing cysteine (residue #198) in the sequence. Both cysteins (#184 & 198) in this newly synthesized cyclic peptide were not modified and remained in their natural position ($^{181}$Asn Asp Val Cys Ala Gln Val His Pro Gln Lys Val Thr Lys Phe Met Leu Cys Ala). (SEQ ID NO:6). As in case of linear peptide, this cyclic peptide was also acetylated at N-terminus and amidated at C-terminus.

Figure 11:
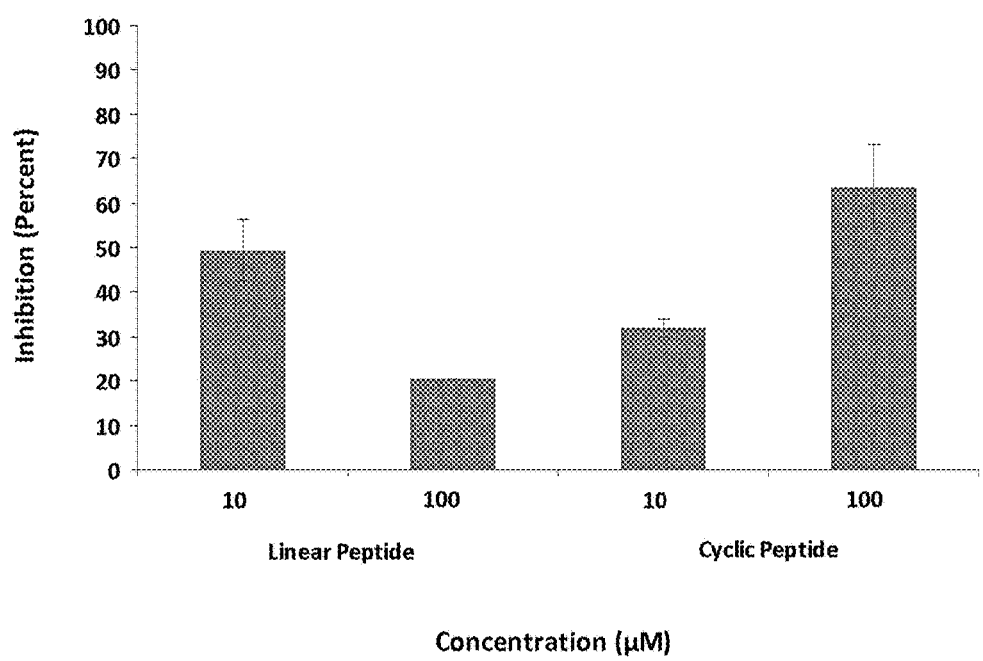
FIG. 11 is a graphical representation of data showing anti-angiogenic activity of a linear peptide (PSA-P3L) of the invention versus a cyclic peptide (PSA-P3C) of the invention.

Linear and cyclic peptides were evaluated for their ability of inhibit HUVEC tube formation in an antiangiogenic assay in Matrigel. The results are shown in FIG. 11 and demonstrate that cyclization of peptide #3 did not alter its physiological properties and inhibited HUVEC tube formation even more efficiently than linear peptide at certain concentrations.

Example 8

The following Example provides a description of our characterization of two putative binding sites for PSA on receptor(s) of Human Umbilical Vein Endothelial cells. Illustrative mass spectroscopy results are shown in FIG. 12. To obtain the data described in this Example and those summarized in FIG. 12 the following materials and methods were used.

1. Biotinylation of f-PSA

The procedure for biotin labeling of proteins is known in the art. In brief, 10 mM of Sulfo-NHS-LC-Biotin (Pierce, Rockford, Ill.) was dissolved in PBS, pH 7.4 and added in 20-fold molar excess to 5 mg of f-PSA and incubated at room temperature for 30 min. Excess reactive biotin was quenched by the adding 1M Tris, pH 7.2 at 1/10th the volume of the biotin labeling reaction, and incubated at room temperature for 10 min. Biotinylated PSA was separated from excess biotin by centrifugation at 2000 rpm using a concentrator with a 10,000 MW cut off membrane (Millipore Corp., Billerica, Mass.). The labeled PSA was aliquoted in 0.5 mL volumes and frozen at −80° C. Biotinylated PSA was detected by ELISA using anti-PSA antibodies and by Western Blot using HRP-conjugated Streptavidin (Pierce, Rockford, Ill., USA).

2. Biotinylated PSA and Isolation of PSA-Target Complexes

The details of the protocol for isolation of receptor targets using biotinylated PSA and crosslinking approach are as follows: Approximately 30×10$^6$ HUVECs were grown on petri dishes (10 cm, BD Falcon, Franklin Lakes, N.J.) to 90% confluency. Media was removed and the cells were washed once with PBS. Cells were incubated with serum free media containing 10 µM biotin labeled PSA and 1:100 (v/v) protease inhibitor cocktail (Sigma, St. Louis, Mo.) for 15 minutes at 4° C. The binding solution was removed and 25 mM of dithiobis[succinimidyl-propionate] (DSP) crosslinker, dissolved in DMSO, was added at final concentration of 10 mM to each dish and incubated for 30 min at room temperature. The crosslinking reaction was stopped by adding 1M Tris, pH 7.2 for a final concentration of 20 mM for 15 minutes at room temperature. Cells were removed from the dishes by using a cell scraper (Costar, Corning, N.Y.) and washed with PBS. Cells collected were centrifuged at 1000 rpm and the supernatant discarded. The cell pellet was lysed using mammalian protein extraction reagent (M-PER) (Pierce, Rockford, Ill.) containing 1:100 (v/v) protease inhibitor cocktail for 15 minutes at room temperature and then centrifuged at 14,000 rpm for 10 minutes. The supernatant was collected to a new tube for further processing. To isolate the PSA-target complex, the cell debris pellet was mixed with non-reducing loading buffer or NP-40 (Sigma, St. Louis, Miss.) at a 1:1 (v/v) ratio and incubated in a 60° C. water bath to re-solubilize membrane proteins, which may contain the biotin labeled PSA crosslinked to the target molecule(s). The supernatant was collected and run on SDS/PAGE, western blot analysis, and probed with streptavidin-HRP for the PSA-target complex. Based on the presence of a band higher than 33 kDa, the re-solublized sample was run on SDS/PAGE, stained with Deep Purple Total Protein Stain (GE Healthcare Life Sciences, Piscataway, N.J.), the band of interest was cut out, and sent for mass spectroscopy analysis.

1. Trypsin Digestion

The solubilized cellular fraction was run under non-reducing conditions on an SDS-PAGE gel, stained with Deep Purple Total Protein Stain (GE Healthcare, Piscataway, N.J.) and scanned using a Typhoon 9410 Imager (GE Healthcare, Piscataway, N.J.). Protein bands of interest were excised manually and placed in 0.6 mL microtube (Axygen, pre-washed with 18 MΩ·cm water (Milli-Q) and methanol). In-gel trypsin digestion was performed according to standard operating procedures routinely used in the Roswell Park Cancer Institute Proteomics Facility. In brief, gel pieces were de-stained with 2000 µL 50% acetonitrile/100 mM ammonium bicarbonate solution for 30 minutes with constant mixing (Mix-Mate, Eppendorf, Hauppauge, N.Y.). After removal of the de-stain solution, gel pieces were dehydrated in 100 µL acetonitrile for 15 minutes at room temperature (RT) and dried in a Speedvac concentrator (Eppendorf, Hauppauge, N.Y.). Dried gel pieces were reduced with 10 mM DTT (Sigma, St. Louis, Miss.)/100 mM sodium bicarbonate solution at RT for 45 minutes. After removal of this solution, samples were alkylated with 200 µL 50 mM iodoacetamide (Sigma, St. Louis, Miss.)/100 mM sodium bicarbonate at RT for 30 minutes under dark conditions. After removal of alkylation solution, samples were washed with 200 µL of 100 mM sodium bicarbonate and incubated with 200 µL of 50% acetonitrile/100 mM sodium bicarbonate at RT for 10 minutes. Samples were dehydrated with 100 µL acetonitrile and dried in a Speedvac concentrator and digested with trypsin (Promega, Madison, Wis., 10 ng/µL in 10% acetonitrile/40 mM sodium bicarbonate, 30-50 µL) at 37° C. for 16 hours. The digests were extracted twice with 100 µL 50% acetonitrile/0.1% TFA at RT for 60 minutes with constant mixing. The extracts were pooled and dried in a Speedvac concentrator and each sample was then reconstituted with 8 µL of 2% formic acid (FA).

3 LC-MS/MS Analysis

Trypsin digested samples (50 µL each) were analyzed by LC nanoelectrospray-tandem mass spectrometry (LC-ESI-MS/MS) using a nanoACQUITY UPLC (Waters Corp, Milford, Mass.) coupled through a nebulization-assisted nanospray ionization source to a Q-ToF Premier mass spectrometer (Waters/Micromass, Milford, Mass.) The LC consisted of a trap column (Symmetry C18, 5μ, 180μ×20 mm, Waters, Milford, Mass.), followed by separation on an analytical column (Atlantis C18, 3μ, 100μ×10 cm, Walters, Milford, Mass.). Samples were loaded, trapped, and washed at a flow rate of 3 μL/min with 98% solvent A (water containing 0.1% FA)/2% solvent B (acetonitrile containing 0.1% FA) for 5 minutes. Peptides were eluted with a gradient of 98% A/2% B to 40% A/60% B for 40 minutes at 0.4 μL/min, 10% A/90% B for 7 minutes at 1.5 μL/minute, and then 10% A/90% B at 1.5 μL/minute for 8 minutes. Throughout the gradient, the mass spectrometer was programmed (Data Dependent Acquisition experiment, DDA) to monitor ions with m/z in the range of 300-1500, and ions with +2 to +4 charges only were selected for MS/MS experiments using the preset DDA collision energy parameters.

4. Database Search and Peptide and Protein Identification

MS/MS spectra were processed and transformed to the PKL file formation using Proteinlynx Global Server v2.3 (Waters/Micromass, Milford, Mass.) and the default parameters of MaxEnt3 (Waters/Micromass, Milford, Mass.). The PKL files were used to search the Homo sapiens subset of the Swiss-Prot database (containing 20,352 sequences) using a locally installed version of MASCOT (Matrix Science, v 2.2.2). The search parameters were as follows: trypsin as the proteolytic enzyme with 2 possible missed cleavages, carboxyamidomethylation of cysteine as a fixed modification, NHS-LC-Biotin of lysine, and 3-(carbamidomethylthio)propanoyl of lysine as a variable modification, the allowable mass error was 100 ppm for peptides and 100 mDa for fragment ions, peptide charge was set to 2+ and 3+, the instrument was set to ESI-QUAD-TOF. The mascot default significance threshold of p<0.05 for assignments was used in the searches and a minimum of two unique peptides were used as a criteria for a match. This example suggests there is/are proteins on the cell membrane that are specific binding sites for intact PSA and that these receptors modulate the biological effect of PSA.

Example 9

The following materials and methods were used in obtaining some of the data presented herein.

Fmoc-Based Solid-Phase Peptide Synthesis: Peptides were prepared by manual solid-phase peptide synthesis. Fmoc groups for Nα protection were cleaved by 8 min treatment with 20% piperidine in DMF followed by the second treatment with the same reagent for 10 min. After the Fmoc cleavage, the rink-resin was washed with DMF (×6). The next residue was then incorporated with the DIPC/HOBt coupling protocol [Fmoc-amino acid (3 equiv), DIPC (3 equiv), and HOBt (3 equiv)]. After gentle agitation (1 hr) and washing with DMF (×6), part of the peptide-resin was subjected to the Kaiser test. On completion of the assembly, the peptide-resin was successively washed with DMF (×3), DCM (×4) and then dried in vacuo.

Cleavage and Deprotection. The cleavage cocktail (Trifluoroacetic acid/H2O=95/5, v/v; 3 ml/100 mg of resin) is added to the washed resin. Complete deprotection was achieved in the cocktail in 4 hrs at 30° C. Following the cleavage reaction, TFA was removed by evaporation.

Disulfide Bond Formation. After cleaved from resin, the crude linear peptide was obtained, which was characterized by RP-HPLC and Maldi-TOF MS. Disulfide formation was realized by oxidation in air (pH~8), which was monitored by RP-HPLC, MS and free sulfhydryl detection (DTNB method).

Purification by Preparative RP-HPLC and Purity Assessment by Analytical HPLC. A crude peptide sample was purified by preparative RP-HPLC (HP1100, Agilent) using a column of Daiso C18 (10 μm, 100 Å, 50×250 mm) A solvent system consisting of solvent A (0.05% TFA, 2% CH3CN in water) and solvent B (90% CH3CN/H2O) at a flow rate of 25 mL/min was used for elution, and the absorbance was detected at 220 nm. The solvent was removed by lyophilization to afford a fluffy powder as a final purified peptide. The chemical structure was characterized by MALDI-TOF-MS, and the purity of the purified material was assessed by analytical HPLC (C18-4.6×250 mm, flow rate of 1 mL/min), and the absorbance was detected at 220 nm.

Example 10

Using peptides made and tested as described above, the data presented in FIGS. 13-21 were obtained. For all these figures, the peptide concentration is 10 uM.

Figure 13:
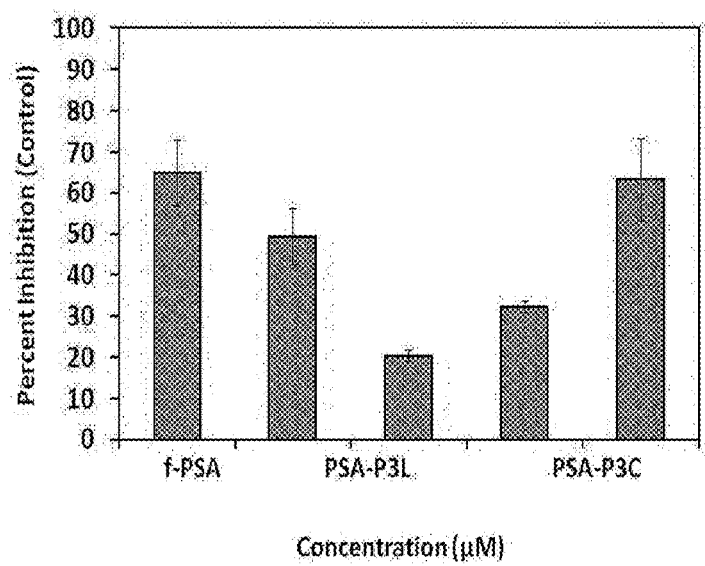
FIG. 13 is a graphical representation of data showing anti-angiogenic activity of f-PSA, PSA-P3L, and PSA-P3C by inhibiting tube formation by HUVEC in a Matrigel assay.

FIG. 13 is a graphical representation of data showing anti-angiogenic activity of f-PSA, PSA-P3L, and PSA-P3C by inhibiting tube formation by HUVEC in a Matrigel assay. To produce the results summarized in FIG. 13, a 24-well tissue culture plate was coated with 200 ul/well of Matrigel and incubated for 30 min at 37 C. Approximately 80,000 HUVEC in 0.5 ml of media supplemented with f-PSA or PSA-P3L, PSA-P3C was applied on top of the Matrigel layer and cells were incubated for 18 hr at 37 C foe endothelial cell tube formation. Live cell images (4× magnification) were taken using Nikon Eclipse TE300 inverted microscope system and analyzed using Spot Advance software program. Five images were taken/well. The images were processed further using Analyze 7.0 (AnalyzeDirect, Inc., Overland Park, Kans.) and Angioquant v1.33 to obtain the average tube length for each image. Percent inhibition is expressed in relation to tube length in untreated control cells.

Figure 14:
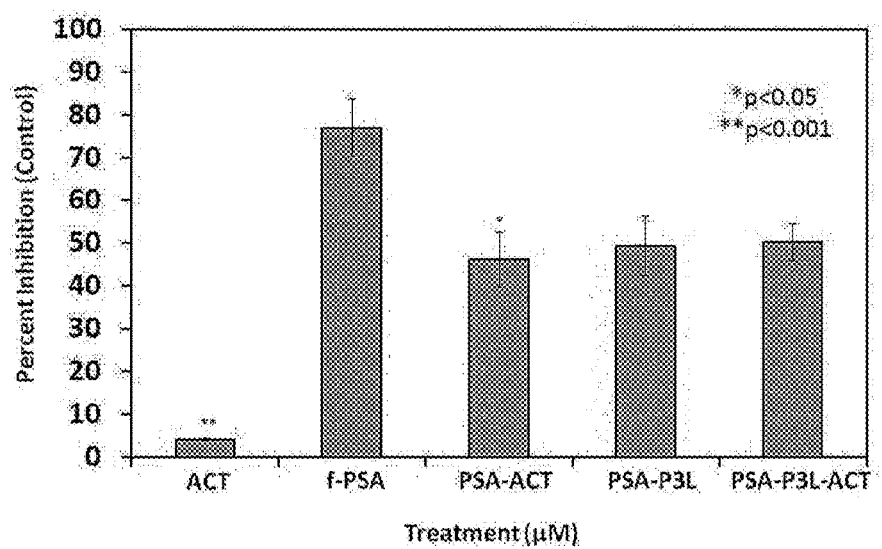
FIG. 14 is a graphical representation of data showing of f-PSA, PSA-ACT Complex, PSA-P3L, and PSA-P3L-ACT complex by inhibiting tube formation by HUVEC in a Matrigel assay.

FIG. 14 is a graphical representation of data showing of f-PSA, PSA-ACT Complex, PSA-P3L, and PSA-P3L-ACT complex by inhibiting tube formation by HUVEC in a Matrigel assay. As can be seen from this Figure, f-PSA has significant anti-angiogenic activity. However, there is a significant loss of anti-angiogenic activity of f-PSA after it complexes with alpha1 anti-chymotrypsin (ACT). On the other hand there is no loss of anti-angiogenic of PSA-P3L in the presence of ACT. The details of anti-angiogenic assay are identical as described above.

Figure 15:
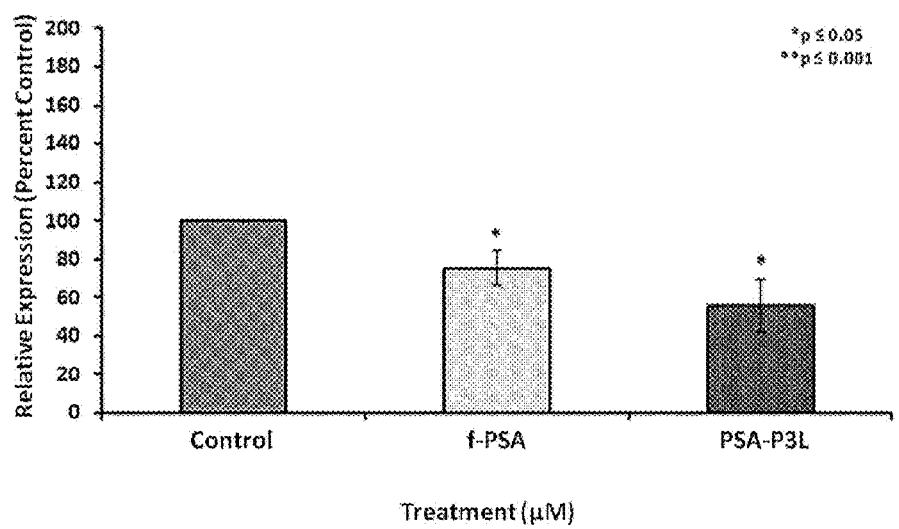
FIG. 15 is a graphical representation of data showing modulation of FLT1 gene expression in HUVEC by f-PSA and PSA-P3l.

FIG. 15 is a graphical representation of data showing modulation of FLT1 gene expression in HUVEC by f-PSA and PSA-P31. As can be seen from this Figure, f-PSA and PSA-P3L effectively inhibit FLT1 gene expression in HUVEC. To obtain the data summarized in this figure, nearly confluent monolayers of HUVEC were treated with 10 uM of f-PSA or PSA-P3L; RNA extracted and reverse transcribed. The c-DNA was amplified by Real-time QPCR using specific primer. The results shown are average of three experiments.

Figure 16:
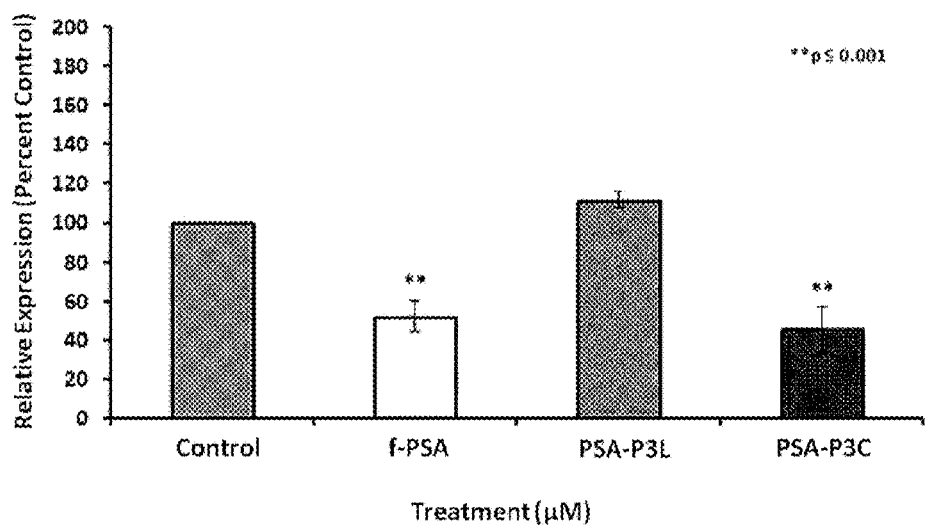
FIG. 16 is a graphical representation of data showing modulation of FAK gene expression in HUVEC by f-PSA and PSA-P3L.

FIG. 16 is a graphical representation of data showing modulation of FAK gene expression in HUVEC by f-PSA and PSA-P3L. To produce the results summarized in FIG. 16, nearly confluent monolayers of HUVEC were treated with 10 uM of f-PSA or PSA-P3L; RNA extracted and reverse transcribed. The c-DNA was amplified by Real-time QPCR using specific primers. The results shown are the average of three experiments. As can be seen from this figure, 16 f-PSA and PSA-P3C significantly down-regulates FAK gene expression in HUVEC. PSA-P3L and control were not significantly different which indicates that cyclic peptide is more effective than linear peptide. The other experimental details are similar to all gene expression studies. Thus, in one embodiment, the invention provides a method for inhibiting FAK gene expression in human endothelial cells comprising contacting the cells with one or more peptides of the invention.

Figure 17:
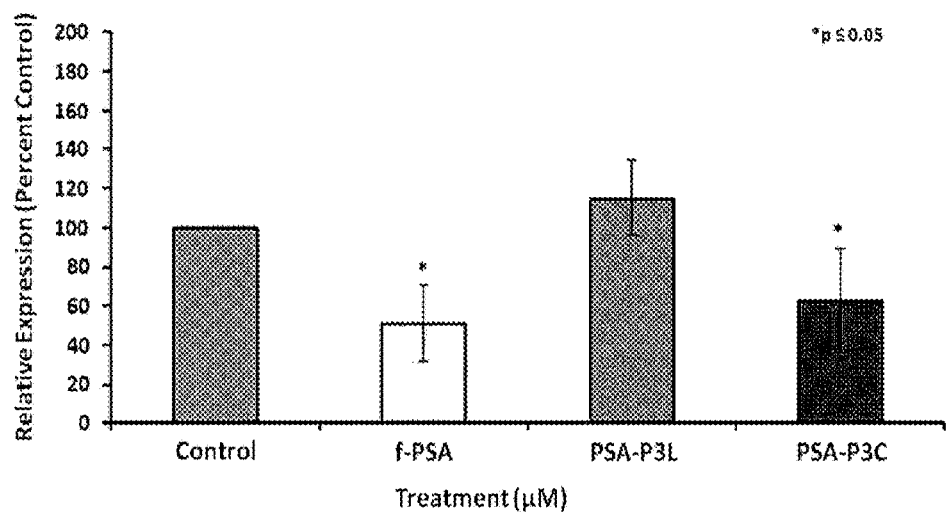
FIG. 17 is a graphical representation of data showing modulation of VEGF gene expression in HUVEC by f-PSA, PSA-P3L and PSA-P3C.

FIG. 17 is a graphical representation of data showing modulation of VEGF gene expression in HUVEC by f-PSA, PSA-P3L and PSA-P3C. To produce the results summarized in FIG. 17, nearly confluent monolayers of HUVEC were treated with 10 uM of f-PSA or PSA-P3L; RNA extracted and reverse transcribed. The c-DNA was amplified by Real-time QPCR using specific primers. The results shown are average of three experiments. PSA-P3L was not significantly different from control. The data represents an average of three experiments. As can be seen from this figure, PSA-P3C and f-PSA significantly down-regulate VEGF gene expression in HUVEC. Thus, in one embodiment, the invention provides a method for inhibiting VEGF expression in human endothelial cells comprising contacting the cells with one or more peptides of the invention.

Figure 18:
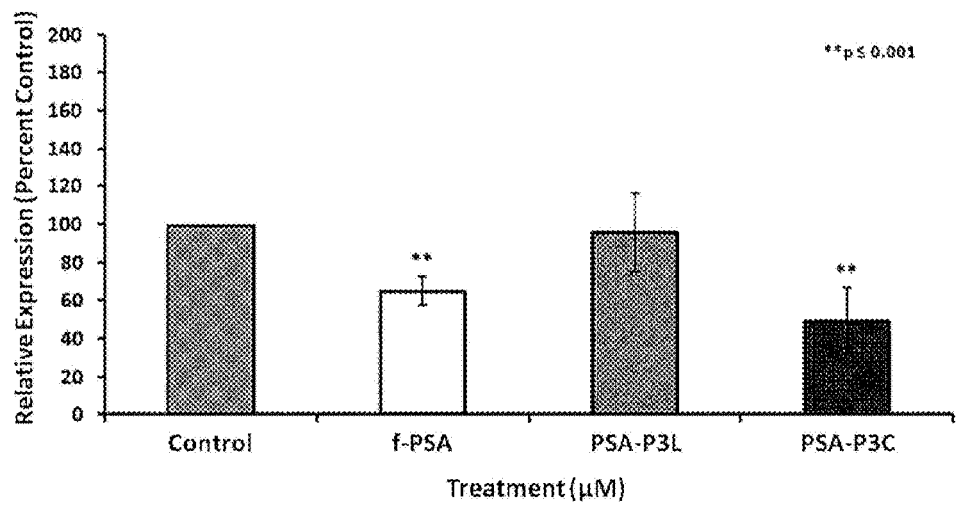
FIG. 18 is a graphical representation of data showing modulation of ANG2 gene expression in HUVEC by f-PSA, PSA-P3l and PSA-P3C.

FIG. 18 is a graphical representation of data showing modulation of ANG2 gene expression in HUVEC by f-PSA, PSA-P31 and PSA-P3C. To produce the results summarized in FIG. 18, nearly confluent monolayers of HUVEC were treated with 10 uM of f-PSA, PSA-P3L or PSA-P3C; RNA extracted and reverse transcribed. The c-DNA was amplified by Real-time QPCR using specific primer. The results shown are an average of three experiments. As can be seen from this figure, f-PSA and PSA-P3C significantly inhibited ANG2 gene expression whereas PSA-P3L was not significantly different from control. Thus, PSA-P3C and f-PSA significantly down-regulate ANG2 gene expression in HUVEC.

Accordingly, in one embodiment, the invention provides a method for inhibiting ANG2 expression in human endothelial cells comprising contacting the cells with one or more peptides of the invention.

Figure 19:
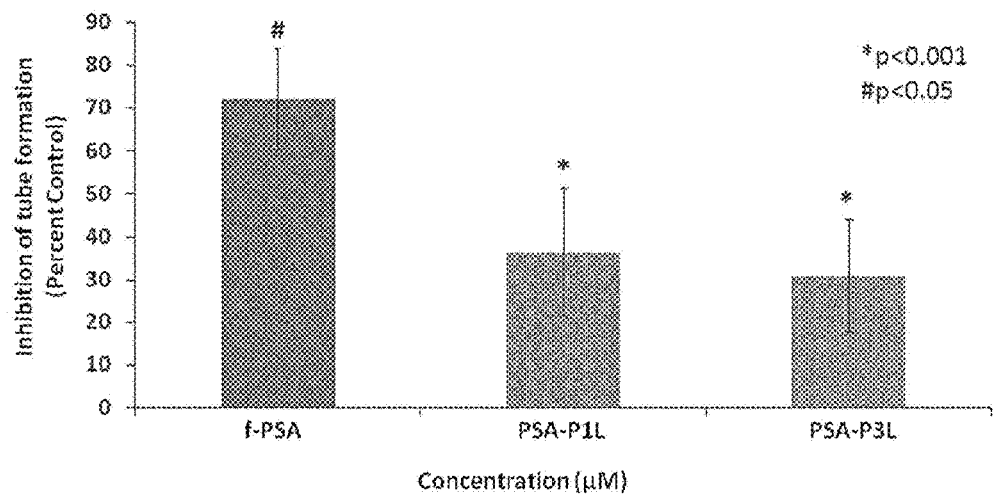
FIG. 19 is a graphical representation of data showing anti-angiogenic activity of f-PSA, PSA-P1L and PSA-P3L via inhibition of tube formation by HUVEC in Matrigel.

FIG. 19 is a graphical representation of data showing anti-angiogenic activity of f-PSA, PSA-P1L and PSA-P3L via inhibition of tube formation by HUVEC in Matrigel. As can be seen from this figure, linear peptides PSA, PSA-P1L and PSA-P3L significantly inhibit HUVEC tube formation in an in vitro anti-angiogenic assay.

Figure 20:
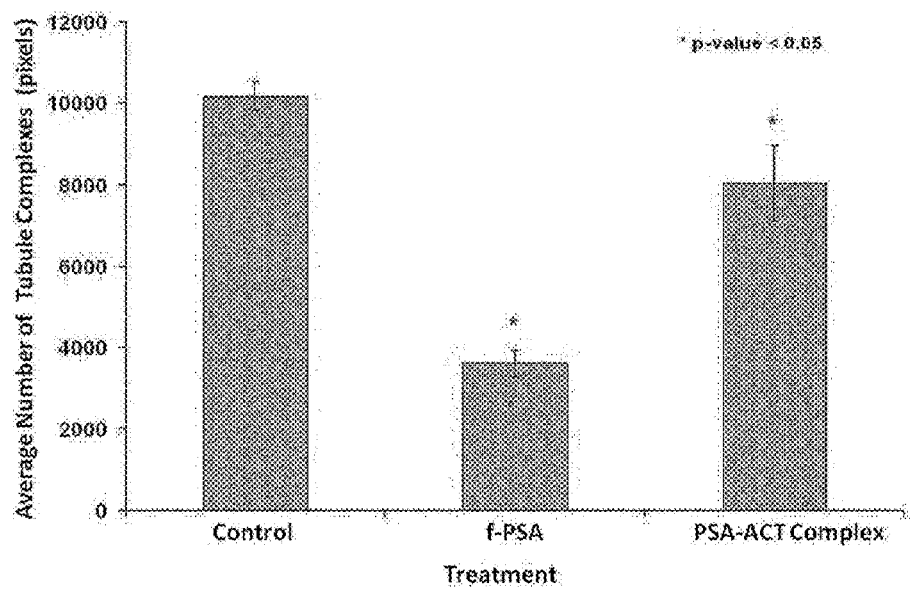
FIG. 20 is a graphical representation of data showing anti-angiogenic activity of f-PSA and PSA-ACT complex via inhibition of tube formation by HUVEC in Matrigel.

FIG. 20 is a graphical representation of data showing anti-angiogenic activity of f-PSA and PSA-ACT complexes via inhibition of tube formation by HUVEC in Matrigel. As can be seen from this figure, f-PSA has significant anti-angiogenic activity. In in vitro anti-angiogenic assay, f-PSA inhibits HUVEC tube formation in Matrigel. However this physiological activity of PSA is significantly reduced when it complexes with serine protease inhibitor, alpha 1, anti-chymotrypsin (ACT). The results shown here are an average of three experiments.

Figure 21:
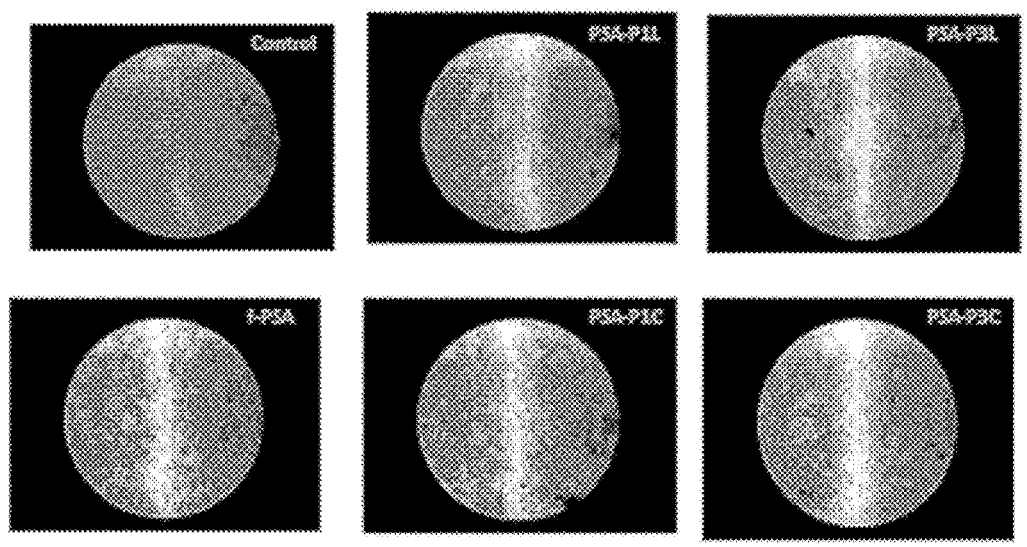
FIG. 21 is photographic representation of the effect of f-PSA, PSA-P1L, PSA-P1C, PSA-P3L and PSA-P3C on migratory properties of HUVEC.

FIG. 21 is photographic representation of the effect of f-PSA, PSA-P1L, PSA-P1C, PSA-P3L and PSA-P3C on migratory properties of HUVEC. To produce the results summarized in FIG. 21, a commercially available CytoSelect 24-well Wound Healing Assay kit was used. Monolayers were disrupted by the plastic insert to produce a linear wound (0.9 mm width), the wells washed with PBS to remove debris, and cultures incubated with f-PSA, PSA-P1l, PSA-P1C, PSA-P3L or PSA-P3C at 10 uM concentration. Wounded fields were measured at 48 hr using phase contrast microscopy to measure wound size.

The foregoing description of specific embodiments is for the purpose of illustration and is not to be construed as restrictive. From the teachings of the present invention, those skilled in the art will recognize that various modifications and changes may be made without departing from the spirit of the invention.

We claim:

1. A method of inhibiting angiogenesis in an individual comprising inhibiting angiogenesis in the individual by administering a composition comprising a peptide to the individual in an amount effective to inhibit the angiogenesis, wherein the peptide is selected from distinct peptides in the group consisting of: a peptide consisting of the sequence Lys Asn Arg Phe Leu Arg Pro Gly Asp Asp Ser Ser His (SEQ ID NO:1), a peptide consisting of the sequence Cys Lys Asn Arg Phe Leu Arg Pro Gly Asp Asp Ser Ser His Cys (SEQ ID NO:7), a peptide consisting of the sequence Asn Asp Val Cys Ala Gln Val His Pro Gln Lys Val Thr Lys (SEQ ID NO:3), a peptide consisting of the sequence Asn Asp Val Ala Ala Gln Val His Pro Gln Lys Val Thr Lys (SEQ ID NO:8), a peptide consisting of the sequence Asn Asp Val Cys Ala Gln Val His Pro Gln Lys Val Thr Lys Phe Met Leu Cys Ala (SEQ ID NO:6), a peptide consisting of the sequence Asn Asp Val Ala Ala Gln Val His Pro Gln Lys Val Thr Lys Phe Met Leu Ala Ala (SEQ ID NO:9), and combinations thereof.

2. The method of claim 1, wherein the inhibition of angiogenesis comprises inhibition of angiogenesis in a tumor in the individual.

3. The method of claim 1, wherein the peptide is cyclic.

4. The method of claim 3, wherein the peptide consists of SEQ ID NO:6, and wherein the two Cys in the sequence of SEQ ID NO:6 are connected to one another via a disulfide bond, or wherein the peptide consists of SEQ ID NO:7, and wherein the two Cys in the sequence of SEQ ID NO:7 are connected to one another via a disulfide bond.

5. The method of claim 1, wherein the composition comprises more than one of the distinct peptides.

* * * * *

SEQUENCE LISTING

```
<160> NUMBER OF SEQ ID NOS: 36

<210> SEQ ID NO 1
<211> LENGTH: 13
<212> TYPE: PRT
<213> ORGANISM: Artificial Sequence
<220> FEATURE:
<223> OTHER INFORMATION: synthetic peptide

<400> SEQUENCE: 1

Lys Asn Arg Phe Leu Arg Pro Gly Asp Asp Ser Ser His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: synthetic peptide

<400> SEQUENCE: 2

Gly Trp Gly Ser Ile Glu Pro Glu Glu Phe Leu Thr Pro Lys Lys Leu
1               5                   10                  15

Gln

<210> SEQ ID NO 3
```

```
<211> LENGTH: 14
<212> TYPE: PRT
<213> ORGANISM: Artificial Sequence
<220> FEATURE:
<223> OTHER INFORMATION: synthetic peptide

<400> SEQUENCE: 3

Asn Asp Val Cys Ala Gln Val His Pro Gln Lys Val Thr Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

Gly Arg Trp Thr Gly Gly Lys Ser Thr Cys Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Ser Glu Pro Cys Ala Leu Pro Glu Arg Pro Ser
1               5                   10

<210> SEQ ID NO 6
<211> LENGTH: 19
<212> TYPE: PRT
<213> ORGANISM: Artificial Sequence
<220> FEATURE:
<223> OTHER INFORMATION: synthetic peptide

<400> SEQUENCE: 6

Asn Asp Val Cys Ala Gln Val His Pro Gln Lys Val Thr Lys Phe
1               5                   10                  15

Met Leu Cys Ala

<210> SEQ ID NO 7
<211> LENGTH: 15
<212> TYPE: PRT
<213> ORGANISM: Artificial Sequence
<220> FEATURE:
<223> OTHER INFORMATION: synthetic peptide

<400> SEQUENCE: 7

Cys Lys Asn Arg Phe Leu Arg Pro Gly Asp Asp Ser Ser His Cys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: synthetic peptide

<400> SEQUENCE: 8

Asn Asp Val Ala Ala Gln Val His Pro Gln Lys Val Thr Lys
1               5                   10
```

<210> SEQ ID NO 9
<211> LENGTH: 19
<212> TYPE: PRT
<213> ORGANISM: Artificial Sequence
<220> FEATURE:
<223> OTHER INFORMATION: synthetic peptide

<400> SEQUENCE: 9

Asn Asp Val Ala Ala Gln Val His Pro Gln Lys Val Thr Lys Phe Met
1               5                   10                  15

Leu Ala Ala

<210> SEQ ID NO 10
<211> LENGTH: 261
<212> TYPE: PRT
<213> ORGANISM: Homo sapiens

<400> SEQUENCE: 10

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 11
<211> LENGTH: 13
<212> TYPE: PRT
<213> ORGANISM: Artificial Sequence
<220> FEATURE:

<223> OTHER INFORMATION: synthetic peptide

<400> SEQUENCE: 11

Lys Ala Arg Phe Leu Arg Pro Gly Asp Asp Ser Ser His
1               5                   10

<210> SEQ ID NO 12
<211> LENGTH: 13
<212> TYPE: PRT
<213> ORGANISM: Artificial Sequence
<220> FEATURE:
<223> OTHER INFORMATION: synthetic peptide

<400> SEQUENCE: 12

Lys Asn Ala Phe Leu Arg Pro Gly Asp Asp Ser Ser His
1               5                   10

<210> SEQ ID NO 13
<211> LENGTH: 13
<212> TYPE: PRT
<213> ORGANISM: Artificial Sequence
<220> FEATURE:
<223> OTHER INFORMATION: synthetic peptide

<400> SEQUENCE: 13

Lys Asn Arg Ala Leu Arg Pro Gly Asp Asp Ser Ser His
1               5                   10

<210> SEQ ID NO 14
<211> LENGTH: 13
<212> TYPE: PRT
<213> ORGANISM: Artificial Sequence
<220> FEATURE:
<223> OTHER INFORMATION: synthetic peptide

<400> SEQUENCE: 14

Lys Asn Arg Phe Ala Arg Pro Gly Asp Asp Ser Ser His
1               5                   10

<210> SEQ ID NO 15
<211> LENGTH: 13
<212> TYPE: PRT
<213> ORGANISM: Artificial Sequence
<220> FEATURE:
<223> OTHER INFORMATION: synthetic peptide

<400> SEQUENCE: 15

Lys Asn Arg Phe Leu Ala Pro Gly Asp Asp Ser Ser His
1               5                   10

<210> SEQ ID NO 16
<211> LENGTH: 13
<212> TYPE: PRT
<213> ORGANISM: Artificial Sequence
<220> FEATURE:
<223> OTHER INFORMATION: synthetic peptide

<400> SEQUENCE: 16

Lys Asn Arg Phe Leu Arg Ala Gly Asp Asp Ser Ser His
1               5                   10

<210> SEQ ID NO 17
<211> LENGTH: 13
<212> TYPE: PRT
<213> ORGANISM: Artificial Sequence
<220> FEATURE:
<223> OTHER INFORMATION: synthetic peptide

<400> SEQUENCE: 17

Lys Asn Arg Phe Leu Arg Pro Ala Asp Asp Ser Ser His
1               5                   10

<210> SEQ ID NO 18
<211> LENGTH: 13
<212> TYPE: PRT
<213> ORGANISM: Artificial Sequence
<220> FEATURE:
<223> OTHER INFORMATION: synthetic peptide

<400> SEQUENCE: 18

Lys Asn Arg Phe Leu Arg Pro Gly Ala Asp Ser Ser His
1               5                   10

<210> SEQ ID NO 19
<211> LENGTH: 13
<212> TYPE: PRT
<213> ORGANISM: Artificial Sequence
<220> FEATURE:
<223> OTHER INFORMATION: synthetic peptide

<400> SEQUENCE: 19

Lys Asn Arg Phe Leu Arg Pro Gly Asp Ala Ser Ser His
1               5                   10

<210> SEQ ID NO 20
<211> LENGTH: 13
<212> TYPE: PRT
<213> ORGANISM: Artificial Sequence
<220> FEATURE:
<223> OTHER INFORMATION: synthetic peptide

<400> SEQUENCE: 20

Lys Asn Arg Phe Leu Arg Pro Gly Asp Asp Ala Ser His
1               5                   10

<210> SEQ ID NO 21
<211> LENGTH: 13
<212> TYPE: PRT
<213> ORGANISM: Artificial Sequence
<220> FEATURE:
<223> OTHER INFORMATION: synthetic peptide

<400> SEQUENCE: 21

Lys Asn Arg Phe Leu Arg Pro Gly Asp Asp Ser Ala His
1               5                   10

<210> SEQ ID NO 22
<211> LENGTH: 13
<212> TYPE: PRT
<213> ORGANISM: Artificial Sequence
<220> FEATURE:
<223> OTHER INFORMATION: synthetic peptide

<400> SEQUENCE: 22

Lys Asn Arg Phe Leu Arg Pro Gly Asp Asp Ser Ser Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: synthetic peptide

```
<400> SEQUENCE: 23

Asn Arg Phe Leu Arg Pro Gly Asp Asp Ser Ser His
1               5                   10

<210> SEQ ID NO 24
<211> LENGTH: 11
<212> TYPE: PRT
<213> ORGANISM: Artificial Sequence
<220> FEATURE:
<223> OTHER INFORMATION: synthetic peptide

<400> SEQUENCE: 24

Arg Phe Leu Arg Pro Gly Asp Asp Ser Ser His
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic peptide

<400> SEQUENCE: 25

Phe Leu Arg Pro Gly Asp Asp Ser Ser His
1               5                   10

<210> SEQ ID NO 26
<211> LENGTH: 9
<212> TYPE: PRT
<213> ORGANISM: Artificial Sequence
<220> FEATURE:
<223> OTHER INFORMATION: synthetic peptide

<400> SEQUENCE: 26

Leu Arg Pro Gly Asp Asp Ser Ser His
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27

Arg Pro Gly Asp Asp Ser Ser His
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic peptide

<400> SEQUENCE: 28

Pro Gly Asp Asp Ser Ser His
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic peptide

<400> SEQUENCE: 29
```

```
Gly Asp Asp Ser Ser His
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic peptide

<400> SEQUENCE: 30

Asp Asp Ser Ser His
1               5

<210> SEQ ID NO 31
<211> LENGTH: 4
<212> TYPE: PRT
<213> ORGANISM: Artificial Sequence
<220> FEATURE:
<223> OTHER INFORMATION: synthetic peptide

<400> SEQUENCE: 31

Asp Ser Ser His
1

<210> SEQ ID NO 32
<211> LENGTH: 11
<212> TYPE: PRT
<213> ORGANISM: Artificial Sequence
<220> FEATURE:
<223> OTHER INFORMATION: synthetic peptide

<400> SEQUENCE: 32

Lys Trp Ile Lys Asp Thr Ile Val Ala Asn Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetic peptide

<400> SEQUENCE: 33

Lys Ser Asp Gly Ile Tyr Ile Ile Asn Leu Lys Arg
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic peptide

<400> SEQUENCE: 34

Thr Trp Glu Lys Leu Leu Leu Ala Ala Arg
1               5                   10

<210> SEQ ID NO 35
<211> LENGTH: 22
<212> TYPE: PRT
<213> ORGANISM: Artificial Sequence
<220> FEATURE:
<223> OTHER INFORMATION: synthetic peptide

<400> SEQUENCE: 35
```

```
Gln Val Ile Leu Thr Leu Gln Pro Thr Leu Val Ala Val Gly Lys Ser
1               5                   10                  15

Phe Thr Ile Glu Cys Arg
            20

<210> SEQ ID NO 36
<211> LENGTH: 17
<212> TYPE: PRT
<213> ORGANISM: Artificial Sequence
<220> FEATURE:
<223> OTHER INFORMATION: synthetic peptide

<400> SEQUENCE: 36

Ala Val Leu Lys Phe Ala Ala Ala Thr Gly Ala Thr Pro Ile Ala Gly
1               5                   10                  15

Arg
```